United States Patent [19]

Cooper

[11] Patent Number: 4,557,934
[45] Date of Patent: Dec. 10, 1985

[54] PENETRATING TOPICAL PHARMACEUTICAL COMPOSITIONS CONTAINING 1-DODECYL-AZACYCLOHEPTAN-2-ONE

[75] Inventor: Eugene R. Cooper, Cincinnati, Ohio

[73] Assignee: The Procter & Gamble Company, Cincinnati, Ohio

[21] Appl. No.: 506,275

[22] Filed: Jun. 21, 1983

[51] Int. Cl.$^4$ .................... A01N 59/26; A61K 33/42
[52] U.S. Cl. .................... 424/128; 424/88; 514/399; 514/947; 514/635; 514/374; 514/159; 514/165; 514/231; 514/270
[58] Field of Search ............... 424/180, 241, 243, 128, 424/251, 250

[56] References Cited

U.S. PATENT DOCUMENTS

| | | | |
|---|---|---|---|
| 1,974 | 1/1879 | Wickett et al. | 424/243 |
| 296,706 | 8/1881 | Cooper | 424/181 |
| 383,391 | 6/1882 | Cooper | 424/239 |
| 506,273 | 5/1883 | Cooper | 425/243 |
| 506,274 | 5/1883 | Cooper et al. | 424/243 |
| 2,990,331 | 6/1961 | Neumann et al. | 424/241 |
| 3,535,422 | 10/1970 | Cox et al. | 424/164 |
| 3,934,013 | 1/1976 | Poulsen | 424/239 |
| 3,989,816 | 11/1976 | Rajadhyaksha | 424/365 |
| 4,006,218 | 2/1977 | Sipos | 424/54 |
| 4,017,641 | 4/1977 | DiGiulio | 424/238 |
| 4,070,462 | 2/1978 | Ecker | 424/243 |
| 4,075,353 | 2/1978 | Mandy | 424/338 |
| 4,126,681 | 11/1978 | Reller | 424/234 |
| 4,132,781 | 1/1979 | Stoughton | 424/240 |
| 4,289,764 | 9/1981 | Yarrow | 424/243 |
| 4,299,826 | 11/1981 | Luedders | 424/181 |
| 4,316,893 | 2/1982 | Rajadhyaksha | 424/180 |
| 4,343,798 | 8/1982 | Fawzi | 424/241 |
| 4,424,210 | 1/1984 | Rajadhyaksha | 424/180 |

FOREIGN PATENT DOCUMENTS

| | | | |
|---|---|---|---|
| 1072009 | 2/1980 | Canada | 424/243 |
| 2514873 | 10/1976 | Fed. Rep. of Germany | 424/243 |
| 1333800 | 11/1968 | United Kingdom | 424/243 |

OTHER PUBLICATIONS

Stoughton, "Enhanced Percutaneous Penetration with 1–Dodecylazacycloheptan-2-one", *Arch. Derm.*, 118, pp. 474–477, (1982).
Rosuold, J. et al., "Effect of Formulation on In Vitro Release and In Vivo Absorption of Corticosteroids from Ointments", *Medd. Novsk Favm Selsk*, 44, 21–45, (1982).
Anjo, D. M. et al., "Methods for Predicting Percutaneous Penetration in Man", *Percutaneous Absorption of Steroids*, pp. 31–51, Academic Press NY, NY, (1980).
CA 92:153,181j.
H. Barnes, et al., *Br. J. Derm.* 93, 459, (1975).
P. J. W. Ayres, et al., *Br. J. Derm.*, 99, 307, (1978).
Schaaf and Gross, *Dermatologica*, 106, 357, (1953).
J. Zatz, et al., *J. Pharm. Sci.*, 67, 789, (1978).
S. K. Chandrasekaran, et al., *J. Pharm. Sci.*, 67, 1370, (1978).
B. Idson, *Cosmetics & Toiletries*, 95, 59, (1980).
M. M. Rieger, *Cosmetics & Toiletries*, 94, 32–37, (1979), and 95, 26–38, (1980).
CA 79: 122,308.

*Primary Examiner*—Elbert L. Roberts
*Attorney, Agent, or Firm*—George W. Allen; Steven J. Goldstein; Jack D. Schaeffer

[57] ABSTRACT

Improved topical pharmaceutical compositions containing a pharmaceutically-active agent and the penetration enhancing agent 1-dodecylazacycloheptan-2-one are disclosed. This agent is used at selected levels in combination with certain $C_3$-$C_4$ diols or a 1-substituted azacycloalkyl-2-one. This composition provides marked transepidermal and percutaneous delivery of the selected pharmaceutically-active agent. A method of treating certain pathologies and conditions responsive to the selected active, systemically or locally, is also disclosed.

23 Claims, No Drawings

PENETRATING TOPICAL PHARMACEUTICAL COMPOSITIONS CONTAINING 1-DODECYL-AZACYCLOHEPTAN-2-ONE

TECHNICAL FIELD

The present invention relates to compositions which enhance the utility of certain pharmaceutically-active agents by effectively delivering these agents through the integument.

BACKGROUND OF THE INVENTION

Because of the ease of access, dynamics of application, large surface area, vast exposure to the circulatory and lymphatic networks, and non-invasive nature of the treatment, the delivery of pharmaceutically-active agents through the skin has long been a promising concept. This is true whether the bioavailability desired is systemic or dermal, regional or local.

The advantages of this form of delivery include, but are not limited to: avoidance of the risks associated with parenteral treatment; elimination of the inconveniences of parenteral treatment; avoidance of the variable rates of absorption and metabolism inherent in oral treatment; increasing the continuity of drug administration by permitting delivery of agents with short biological half-lives; and elimination of gastrointestinal irritation resulting from exposing the gastrointestinal tract to pharmaceutical actives, preservatives, tableting agents, and the like. Most importantly, topical delivery possesses the potential for effectively treating conditions which are local in nature (or which exhibit local manifestations), systemically as well as locally with the same treatment regimen. Thus, effective compositions to deliver pharmaceutical agents are highly sought after.

However, because it must serve as a barrier to the ingress of pathogens and toxic materials, and the egress of physiologic fluids, the skin is highly impermeable. It must be impermeable to preserve its own integrity while at the same time maintaining the delicate dynamic electrolyte balance of the body. The skin must serve a containment function; it must also function as a microbial, chemical, radiation and thermal barrier.

A good deal of this impermeability of the skin results from the nature of one very thin layer created by normal developmental and physiological changes in the skin. After cells are formed in the basal layer, they begin to migrate toward the skin surface, until they are eventually sloughed off. As they undergo this migration, they become progressively more dehydrated and keratinized. When they reach the surface, just prior to being discarded, they form a thin layer of dense, metabolically inactive cells approximately ten microns (10-15 cells) thick. This layer is called the stratum corneum, or the "cornified layer". As a result of the high degree of keratinization of the cells which comprise the stratum corneum, a formidable barrier is created. Therefore, penetration via the nonpolar route, i.e., across the membrane of these cells, remains most difficult.

Other possible penetration routes are available. First, any mechanism which allows the egress of materials, e.g. the sebaceous apparatus, can be manipulated to allow the ingress of materials. Second, the stratum corneum, though keratinized to a great degree, is composed of about 15% lipid-based intercellular material. While it has been noted that this may offer a less formidable route despite the close packing of the cells, the integrity of the skin, and particularly the stratum corneum, has detracted from the overall promise of percutaneous delivery.

Accordingly, in an effort to take advantage of this route of administration and overcome the obstacles the skin naturally provides, the art has turned to the use of specifically selected vehicles and carriers into which the pharmaceutical active is incorporated so that the vehicle or carrier aids in, or at a minimum does not adversely affect, the penetration of the selected active. The art recognizes that to a vast degree the rate of percutaneous delivery of a pharmaceutical active can be significantly decreased by the selection of an improper vehicle.

One of the newest compounds thought to increase the permeability of the skin, when used as or within a vehicle, is the compound 1-dodecyl-azacycloheptan-2-one (Azone). Azone is a colorless and virtually odorless compound of the formula

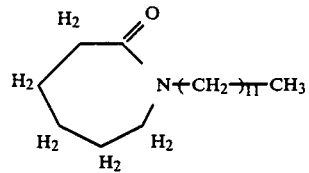

It is reported to have a low order of toxicity with a lethal dose for 50% survival ($LD_{50}$) in the range of about 8 g/kg in rats. The compound is stable over a period of approximately four years.

Azone has been demonstrated to enhance the cutaneous penetration of clindamycin phosphate, erythromycin base, fusidate sodium, fluorouracil, desonide, amcinonide and triamcinolone acetonide. Other n-substituted-azacycloheptan-2-ones of the formula

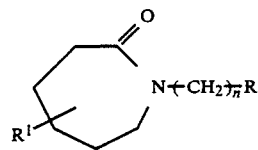

wherein R is a straight or branched chain alkyl group having 1-18 carbon atoms or an aryl group, e.g., phenyl, $R^1$ is H or a lower alkyl group having 1-4 carbon atoms, and n is 0 or a positive integer from 1-10, are also known to aid in the penetration of topically administered physiologically active agents. These compounds have also been described as being useful in aiding in the penetration of certain anti-bacterial agents, antibiotics (particularly lincomycin, clindamycin, tetracycline and erythromycins), steroids, anti-fungal agents, iododeoxyuridine, sunscreens and allergens.

It has now been discovered that the penetration-enhancing efficacy of 1-dodecyl-azacycloheptan-2-one can be significantly improved when it is used in a select, binary combination with certain other penetration-enhancing agents or polar solvents. Specifically, it has been discovered that a binary penetration system comprising Azone in combination with a diol, certain other n-substituted-alkyl-azacycloalkyl-2-ones, or mixtures thereof, consistently and dramatically demonstrates improved topical delivery of certain pharmaceutically-active agents, such as steroids, when the second component is used at specific levels and when the components of the binary combinations are present at specific ratios.

U.S. Pat. No. 3,989,816, Rhaadhyaksha, issued Nov. 2, 1976, discloses a method for enhancing the penetration of pharmaceutical actives through the skin or membranes comprising dissolving an effective amount of the selected agent in a carrier containing a 1-substituted-azacycloheptan-2-one, and, in turn, contacting the skin or membrane with the resulting composition. The actives specifically disclosed include antibacterial agents, antibiotics, steroids, antifungals, allergens, and sunscreens. The specification describes a host of "typical inert carriers" appropriate for formulating a vehicle which contains this compound. These inert carriers include water, acetone, isopropyl alcohol, Freons, ethyl alcohol, polyvinylpyrrolidone, and propylene glycol, as well as polysorbates and tweens.

Stoughton, "Enhanced Percutaneous Penetration with 1-dodecylazacycloheptan-2-one", Arch. Derm., 118, pp. 474–477 (1982), discusses the ability of Azone to aid in the penetration of clindomycin phosphate, erythromycin base, fusidate sodium, fluoroucil, desonide, amcinonide, and triamcinolone acetonide. He states that vehicles such as dimethyl sulfoxide, dimethyl acetamide, dimethyl formamide, 1-methyl-2-pyrrolidone and propylene glycol and "grossly influence" the penetration of an agent through the stratum corneum into the corium.

U.S. Pat. No. 4,132,781, Stoughton, issued Jan. 2, 1979, discloses topical antibacterial compositions containing an antibiotic (of the erythromycin family) in combination with 2-pyrrolidone or an n-lower alkyl-2-pyrrolidone which are useful in the treatment of acne.

U.S. Pat. No. 4,017,641, DiGiulio, issued Apr. 12, 1977, describes skin conditioning compositions containing 2-pyrrolidone. A composition is disclosed which further contains 2.5% propylene glycol.

It is known that certain binary skin penetration systems can increase the disorder of lipids in the skin. By so increasing the disorder of the lipid portion of the cell-envelope in the stratum corneum, the lipid packing of the cells can be disrupted. This disruption allows certain pharmaceutically active agents to pass through the stratum corneum. This discovery has been confirmed by differential scanning calorimetry, indicating that certain binary skin penetration enhancement systems eliminate the Tm-2 peak associated with melting of cell-envelope lipids. This U.S. patent application Ser. No. 296,706, Cooper, et al., filed Aug. 27, 1981, describes compositions for topical application. These compositions are described as suitable for effective delivery of lipophilic, pharmacologically-active compounds using primary alcohols or various carboxylate compounds in combination with selected diols. See European Patent Application No. 43,738, published Jan. 13, 1982.

U.S. Pat. No. 4,343,798, Fawzi, issued Aug. 10, 1982, describes topical antimicrobial/anti-inflammatory compositions containing $C_5-C_{12}$ fatty acids in combination with corticosteroids.

U.S. Pat. No. 3,934,013, Poulsen, issued Jan. 20, 1976, describes topical pharmaceutical compositions containing at least two corticosteroids, propylene glycol, a fatty alcohol and water. The patenee describes the "fatty alcohol ingredient" as any fatty alcohol having from 16–24 carbon atoms and, preferably, as a saturated, monohydric primary alcohol such as cetyl alcohol, stearyl alcohol or behenyl alcohol.

U.S. Pat. No. 4,289,764, Yarrow, et al., issued Sept. 15, 1981, describes topical pharmaceutical compositions with increased shelf stability. These compositions comprise a steroid, 15–50% by weight propylene glycol and are buffered to a pH of 2.7–3.3. The specification describes the desirability of thickening the propylene glycol (due to its low viscosity) with a compound selected from long-chain paraffins, fatty alcohols, and waxes, including cetyl stearyl alcohol, white soft paraffin and liquid paraffin.

U.S. Pat. No. 4,070,462, Ecker, issued Feb. 24, 1978, discloses a topical vehicle which includes (i) 5–15% 1,2-propanediol, 2,3-butanediol or 2methyl-2,4,-propanediol; (ii) 1–3% propylene glycol monostearate; and (iii) petrolatums and waxes to 100%.

U.S. patent application Ser. No. 001,974, Wickett, et al., filed Jan. 8, 1979, now abandoned describes compositions useful in the treatment of acne. These compositions contain benzoyl peroxide, $C_6-C_{14}$ primary alcohols, and a diol selected from 1,2-propanediol, 1,2-butanediol, 1,3-butanediol, and 2,3-butanediol. A foreign equivalent of this application was made available to the public July 23, 1980. See European Patent Application No. 13,459.

U.S. patent application Ser. No. 383,391, Cooper, filed June 1, 1982, now abandoned discloses and claims a binary penetration system utilizing a diol and a cell-envelope disordering compound to aid in the penetration of 9-hydroxyethoxymethyl (and related) derivatives of 6- and 2,6-substituted purines. These compounds are reported to be effective in the treatment of viral infections, especially herpes.

1,2-propanediol ("propylene glycol") and the $C_{10}-C_{14}$ alcohols have been used, separately, in cosmetic and pharmaceutical formulations. In particular, propylene glycol has been described in several articles in the literature as enhancing the penetration of certain pharmacologically active agents, such as the corticosteroids. See Rosuold, J., et al., "Effect of Formulation On In Vitro Release and In Vivo Absorption of Corticosteroids from Ointments", Medd. Novsk Favm Selsk, 44, 21–45 (1982); see also, Anjo, D. M., et al., "Methods for Predicting Percutaneous Penetration in Man", Percutaneous Absorption of Steroids. pp 31–51, Academic Press, New York, N.Y. (1980), both incorporated herein by reference.

U.S. Pat. No. 3,535,422, Cox, et al., Oct. 20, 1970, relates to stable benzoyl peroxide compositions containing organic emollients. The compositions include emollients selected from the $C_4-C_{20}$ aliphatic alcohols, $C_2-C_3$ glycols, $C_{12}-C_{20}$ fatty acids and their esters, and mixtures thereof.

U.S. Pat. No. 4,070,462, Ecker, issued Jan. 24, 1978, describes topical steroid compositions containing 6% propylene glycol and 1% propylene glycol monostearate.

Canadian Pat. No. 1,072,009, Sipos, issued Feb. 19, 1980, describes topical antimicrobial compositions containing $C_5-C_{10}$ straight chain alcohols or $C_{17}$ branched chain alcohols in which the longest chain is $C_5-C_{10}$.

CA 92:153,181j; describes an indomethacin ointment containing 10% propylene glycol and 1.1% diisopropanolamine.

U.S. Pat. No. 2,990,331, Neumann, et al., issued June 27, 1961, describes tetracycline compositions containing carboxylic acid alkylolamides.

H. Barnes, et al., Br. J. Derm. 93, 459 (1975), describe testing of fluocinonide and fluocinolone acetonide in a vehicle described as fatty alcohol propylene glycol (FAPG).

P. J. W. Ayres, et al., *Br. J. Derm.*, 99, 307 (1978), report comparative skin penetration of cortisol from commercially available cortisol ointments.

Schaaf and Gross, *Dermatologica*, 106, 357 (1953), note that unsaturated fatty acids and $C_6$-$C_{14}$ saturated fatty acids are particularly active in provoking epidermal thickening.

J. Zatz, et al., *J. Pharm. Sci.*, 67, 789 (1978), describe the effect of formulation factors on penetration of hydrocortisone through mouse skin.

S. K. Chandrasekaran, et al., *J. Pharm. Sci.*, 67, 1370 (1978), discuss the pharmacokinetics of drug permeation through human skin.

B. Idson, *Cosmetics & Toiletries*, 95, 59 (1980), states that the factors affecting drug penetration and, consequently, in most cases, effectiveness, are complex. He observes that the vehicle that provides ideal conditions for one drug may prove unsatisfactory for another. The author concludes that prediction is not simple and product suitability must be assessed by human trials. The same article indicates that Synalar Cream, a topical corticosteroid preparation, contains sorbitan monooleate and propylene glycol.

M. M. Rieger, *Cosmetics & Toiletries*, 94, 32–37 (1979) and 95, 26–38 (1980), provides a review of current literature in the area of skin penetration.

U.S. Pat. No. 4,299,826, Luedders, issued Nov. 10, 1981, describes a composition for the treatment of acne by using diisopropyl sebacate as a penetration enhancer for an erythromycin derivative in combination with an alcohol.

U.S. Pat. No. 2,990,331, Neumann, et al., issued June 27, 1961, describes the parenteral administration of tetracycline salts from a stable aqueous solution.

CA 79: 122,308, describes an electromagnetic study of n-alkyl ionic surfactants as aiding in human epidermis penetration.

SUMMARY OF THE INVENTION

The present invention relates to improved compositions and methods for the percutaneous delivery of pharmaceutically-active agents to human and animal tissue and systems. The invention provides penetrating topical compositions and therapies, and is based on the use of a pharmaceutically-active agent dissolved in, or admixed with, a novel penetration-enhancing vehicle. The vehicle comprises a binary mixture of 1-dodecylazacycloheptan-2-one and a compound selected from a diol or a second, N-substituted azacycloalkyl-2-one (a "cycloketo compound"). Mixtures of diol/cycloketo compounds may also be employed. The compositions are preferably substantially free of any additional polar lipids, solvents, cosolvents, or excipients which interfere with the penetration of the selected active.

The compositions of this invention comprise a safe and effective amount of a pharmaceutically-active agent, together with a penetration-enhancing vehicle containing a binary mixture of 1-dodecylazacycloheptan-2-one, and a $C_3$-$C_4$ diol, such a propylene glycol, or a second N-substituted azacycloalkyl-2-one of the general formula

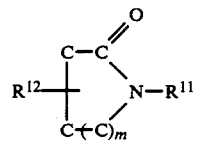

wherein $R^{11}$ is selected from the group consisting of —H, —$CH_3$, —$C_2H_5$, —$C_2H_4OH$, —$C_3H_7$, —$C_3H_6OH$, or —$CH_2CHOHCH_2OH$, $R^{12}$ is —H, —$CH_3$, —$C_2H_5$, —$C_3H_7$, —$C_4H_9$, and m is an integer from 0–2, such as 1-(hydroxyethyl)-azacycloheptan-2-one. The final composition is preferably substantially free of straight chain saturated $C_{16}$-$C_{20}$ primary alcohols and $C_4$-$C_{20}$ mono- or dicarboxylic acids. These compositions can be formulated to deliver actives at levels and rates useful in local or systemic treatment. Employing this binary mixture uniquely increases the effectiveness of 1-dodecylazacycloheptan-2-one as a penetration aid, allowing it to be used at lower levels, or with significantly improved efficacy at equivalent levels.

The invention also encompasses treatment regimens for conditions, or the pain, inflammation, or other pathologies or risks associated with such conditions, which are responsive to the active or actives selected for incorporation into the binary vehicle comprising topically administering to a human or lower animal in need of such treatment a safe and effective amount of the composition. The composition is applied at the afflicted sitis when the condition being treated is responsive to local treatment regimens. When systemic effects and performance are desired, the composition is applied at the afflicted situs, an application situs, or both.

DETAILED DESCRIPTION OF THE INVENTION

By "topical administration", as used herein, is meant directly laying or spreading upon epidermal tissue, especially outer skin or membrane, including the skin or membrane of the oral or vaginal cavities.

By "safe and effective amount", as used herein, is meant a sufficient amount of the composition to provide the desired systemic effect and performance, or local activity, or both, at a reasonable benefit/risk ratio attendant any medical treatment. Within the scope of sound medical judgment, the amount of pharmaceutical active used will vary with the particular condition being treated, the severity of the condition, the duration of the treatment, the specific compound employed, its concentration, the condition of the patient, concurrent therapies being administered, and like factors within the specific knowledge and expertise of the patient or the attending physician.

By "toxicologically- or pharmaceutically-acceptable", as used herein, is meant the pharmaceutical actives, as well as the other compatable drugs, medicaments or inert ingredients which the term describes, are suitable for use in contact with the tissues of humans and lower animals without undue toxicity, irritation, allergic response, and the like, commensurate with a reasonable benefit/risk ratio.

By the term "comprising", as used herein, is meant that various other compatible drugs and medicaments, as well as inert ingredients, occlusive agents, and cosmetic vehicles, can be conjointly employed in the compositions and methods of this invention, as long as the critical binary penetration enhancement vehicle and pharmaceutical active are used. The term "comprising" thus encompasses and includes the more restrictive terms "consisting of" and "consisting essentially of" which characterize the use of the essential ingredients in the manner disclosed herein.

By "afflicted situs", as used herein, is meant a localized area of pathology, discomfort, infection, inflammation or lesion, and the immediately surrounding area.

By "application situs", as used herein, is meant a site suitable for application via a mechanical sustained release device or dressing, e.g., behind the ear, on the arm, back, top of the foot, etc.

By "penetration-enhancing", as used herein, is meant that the binary penetration enhancing compositions of this invention provide marked transepidermal or percutaneous delivery of an incorporated active, when compared to other compositions at equal chemical potential. This latter aspect is important, since varying solubilities of drugs in different vehicles will necessarily affect their transport across skin. Thus, for example, if a drug is soluble in vehicle A to the extent of 24%, and in vehicle B to the extent of 4%, were the compositions to be compared at equal percentage concentration, rather than equal chemical potential, the lower solubility carrier will show a misleading six-fold difference in transport over the more soluble vehicle. The simplest way of assuring equal chemical potential for evaluating penetration enhancement is to use saturated solutions or solutions of equal percentage of saturation of pharmacological active in the various vehicles.

By "substantially free", as used herein, is meant that the penetration-enhancing compositions of the present invention contains less than about 10%, preferably less than 3.5%, more preferably less than about 1%, and most preferably less than about 0.5%, of any specific compound, or member of the group of compounds, described by this term.

As used herein, all percentages and ratios are by weight of the total composition unless otherwise specified.

The terms "active", "pharmaceutical active", "pharmacological active", "pharmaceutical agent", "pharmacological agent", "pharmaceutically-, or pharmacologically-active agent", "chemical agent", and "therapeutic agent", are used interchangably herein.

The compositions of this invention require, at a minimum, a pharmaceutically-active agent capable of producing systemic effects, or producing or possessing local activity, in a binary vehicle or carrier comprising 1-dodecylazacycloheptan-2-one and a diol, an N-substituted azacycloalkyl-2-one, or mixtures of these latter two components. The compositions of this invention may additionally contain other optional components which reduce skin irritation, or enhance their cosmetic appeal and acceptability, i.e., thickeners, pigments, fragrances, perfumes and the like. The compositions are preferably substantially free from penetration-interfering polar lipids, solvents, cosolvents or excipients, particularly $C_{16}$-$C_{20}$ saturated primary alcohols, and $C_4$-$C_{20}$ mono- or dicarboxylic acids.

VEHICLE

The vehicles of the present invention significantly enhance the penetration of a host of pharmaceutically-active agents. They comprise, at a minimum, 1-dodecylazacycloheptan-2-one in combination with a diol compound or a second N-substituted alkyl-azacycloalkyl-2-one (a cycloketo compound). Mixtures of diol compounds, cycloketo compounds, or mixtures of diols and cycloketo compounds may also be employed. The 1-dodecylazacycloheptan-2-one component of the present invention is present at a level of about 0.9% to about 40%, by weight of the composition, preferably about 1% to about 35%, and more preferably about 2% to about 10%. 1-dodecylazacycloheptan-2-one is most preferably present at a level of about 2% to about 5%, by weight of the composition.

The diol compounds useful in the compositions and methods of the instant invention include 1,2-propanediol, 1,3-propanediol, 1,2-butanediol, 1,3-butanediol, 1,4-butanediol, 2,3-butanediol or mixtures of these diol compounds. 1,2-propanediol and 1,2-butanediol are preferred diol compounds. 1,2-propanediol is an especially preferred diol compound. These diol compounds are items of commerce.

The "cycloketo" compounds useful in the compositions and methods of the present invention are of the general formula:

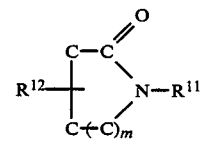

wherein $R^{11}$ is selected from the group consisting of —H, —$CH_3$, —$C_2H_5$, —$C_2H_4OH$, —$C_3H_7$, —$C_3H_6OH$, or —$CH_2CHOHCH_2OH$, $R^{12}$ is —H, —$CH_3$, —$C_2H_5$, —$C_3H_7$, —$C_4H_9$, and m is an integer from 0-2. Preferred cycloketo compounds are of the above formula where $R^{11}$ is —H or —$C_2H_4OH$, $R^{12}$ is —H, and m=0; i.e., pyrrolidone and 1-(2-hydroxyethyl)-azacyclopentan-2-one. The synthesis and preparation of these "cycloketo" compounds, as well as 1-dodecylazacycloheptan-2-one, is well within the skill of the art, as represented by and described in U.S. Pat. No. 3,989,816, Rajadhyaksha, issued Nov. 2, 1976, incorporated herein by reference.

The diol compounds, cycloketo compounds, or mixtures thereof, are generally present at a level of about 15% to about 99%, by weight of the composition, and preferably about 20% to about 99%. The diol compounds, cycloketo compounds, or mixtures thereof, are most preferably present at a level of about 25% to about 96%, by weight of the composition.

Binary mixtures of 1-dodecylazacycloheptan-2-one, and any of the foregoing diol compounds, cycloketo compounds or mixtures thereof, in a weight:weight ratio of diol compound:1-dodecylazacycloheptan-2-one or of cycloketo compound:1-dodecylazacycloheptan-2-one of from about 1:5 to about 100:1 provide significant enhancement of penetration for topical pharmaceutically-active agents, especially those described herein. A ratio of diol compound:1-dodecylazacycloheptan-2-one or cycloketo compound:1-dodecylazacycloheptan-2-one of from about 3:1 to about 100:1 is preferred.

The compositions of this invention typically contain from about 15.9% to about 99.9%, by weight of the composition, and preferably about 20% to about 99.9%, by weight of the composition, of the penetration enhancing mixture of the diol/cycloketo compounds and 1-dodecylazacycloheptan-2-one, employing the levels and ratios described above.

PHARMACEUTICALLY-ACTIVE AGENTS

The compositions of the present invention may be formulated to incorporate pharmaceutically-acceptable or pharmaceutically-active agents which are useful in providing activity to the following "targets": (1) at the surface of the skin; (2) in the stratum corneum itself; (3) in the viable epidermis and upper dermis, just below the stratum corneum; (4) in the various glands and structures in and beneath the dermis (e.g., subcutaneous adipose, dermal vasculature); and/or (5) the general system (i.e., produce systemic effects). While the compositions of the present invention are capable of providing remarkably effective levels and rates of percutaneous delivery, they are also capable of providing surface effect. Since many skin conditions are stratified in either origin or involvement, any therapeutic treatment must accordingly possess the capability of treating the condition at the skin surface as well as at and below the stratum corneum. This is particularly true of topical antimicrobial and antiseptic therapies (as well as the effective use of sunscreens). The stratum corneum may also be a useful target (it may be either treated or removed) in the treatment of, for example, psoriatic scales, corns, callouses and dandruff. Skin glands are an appropriate target in, for example, the treatment of acne.

However, it is the accessibility of "targets" (3), (4) and (5), above, which make the compositions of the present invention particularly useful, i.e., those sites or areas below the stratum corneum.

When the "target" lies beneath the stratum corneum, topical therapy with conventional formulations becomes quite complicated and unpredictable. Whether the "target" is the viable tissue immediately below the stratum corneum, or whether a true systemic effect is sought, conventional vehicles are not generally successful or predictable. Many potentially useful topical drugs have not been employed in topical treatment because of the inability of most topical systems to deliver the drug to the desired target in sufficient amounts, or at a sufficient rate, to provide clinical utility.

A second significant drawback to conventional methods of topical delivery of drugs is the significant variation in skin between individuals, or even at different locations on the body of the same individual. Differences in age, health, and weather, and the natural biological variation of the integument within the same individual, make topical treatment of conditions requiring delivery to a "target" below the stratum corneum unpredictable.

The compositions of the present invention minimize such variation and allow topical treatment to be employed where it is necessary to deliver to "targets" below the stratum corneum with certainty.

Accordingly, a host of pharmaceutically-active agents are useful in the compositions of the present invention. Such agents include, without limitation, antimicrobials, including sulfonamides, sulfones, natural and synthetic antibacterial agents, beta-lactum antibiotics, non-lactam antibiotics, antimyobacterial agents, antimalarials (including antifolates), antiamebic agents, agents effective against trypanosomiasis and other protozoan diseases, anthelmintic agents, antifungal agents, antiviral agents, neoplastic agents, agents affecting the immune response, blood calcium regulators, peptide and protein hormones, male sex hormones and their analogues, female sex hormones and their analogues, agents useful in blood glucose regulation, anticoagulents, antithrombotics and hemostatics, antihyperlipidemic agents, cardiac drugs, thyromimetic and antithyroid drugs, adrenergics, antihypertensive agents, cholinergics, anticholinergics, antispasmodics, antiulcer drugs, skeletal and smooth muscle relaxants, histamine $H_2$-receptor agonists and antagonists, prostaglandins, general inhibitors of the allergic response, antihistamines, local anesthetics, analgesics, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, bone-active agents (e.g., organodiphosphonates), antiarthritics, vitamins, diagnostic agents and sunscreens. Such agents can be used for systemic effects, local activity, or both, as appropriate and desired. Examples of such pharmaceutically-active agents are well-known to the skilled artisan. They can be found, for example, in U.S. Pat. No. 3,989,816, Rajadhyaksha, issued Nov. 2, 1976; Stoughton, R. B., "Enhanced Percutaneous Penetration with 1-Dodceylazacycloheptan-2-one", *Arch Dermatol*, 118, pp. 474–477 (1982); U.S. Pat. No. 4,343,798, Fawzi, issued Aug. 10, 1982; European Patent Application No. 43,730, published Jan. 13, 1982; U.S. Pat. No. 4,199,475, Schaeffer, issued Apr. 22, 1980; Miller and Munro, *Drugs*, 19, 119–134 (1980); all of which are expressly incorporated herein by reference. Standard texts such as Goodman, et al., *The Pharmacological Basis of Therapeutics*, 5th Ed., MacMillan Publishing Co., Inc., New York (1975), Anderson, et al., *Remington's Pharmaceutical Sciences*, 15th Ed., Mack Publishing Co., Easton, Pennsylvania (1975), and Wolfe, *Burger's Medicinal Chemistry*, 2, 3, 4th Ed., John Wiley and Sons, New York, N.Y. (1981), both incorporated herein by reference, may also be used to determine the use, synthesis, side-effects, etc., of such pharmaceutically-active agents.

The pharmaceutically-active agents may be used in the compositions and methods of the present invention at any safe and effective level, or in any safe and effective amount. The pharmaceutically-active agents useful in the compositions and methods of the present invention may be incorporated at levels of about 0.01% to about 30%, by weight of the composition, and are preferably present at levels of about 0.01% to about 10%, by weight of the composition. Such agents are more preferably present at a level of about 0.05% to about 10%, and most preferably present at a level of about 0.5% to about 5%, by weight of the composition. In a highly preferred embodiment, the compositions of the present invention contain about 1% to about 5% of the pharmaceutically-active agent, by weight of the composition. However, it will be appreciated that the level of active useful in the compositions and methods of the present invention will depend on a variety of factors, including the nature and activity of the agent, the desired effect (systemic, local or both types), possible adverse reactions, the ability and speed of the agent selected to reach its intended target, the cost and availability of the agent, the use of two or more pharmaceutically-active agents, and other factors within the particular knowledge of the patient and physician. In some instances, the levels discussed above are not appropriate for a particular active, or a particular class of actives; thus a more appropriate level will be suggested herein.

The following lists of actives are not intended to be limiting.

The compositions of the present invention are effective in the percutaneous delivery of anti-inflammatory agents, particularly steroidal and non-steroidal anti-inflammatory agents.

Steroids, particularly the adrenal corticosteroids and their synthetic analogues, are some of the most useful pharmaceutical actives known in the art. These compounds have the capacity to prevent the development of, or suppress existing, localized heat, redness, tenderness and swelling which characterizes any inflammation of the skin or mucous membranes. The utility of these compounds is magnified in a clinical setting by the fact that corticosteroids inhibit this inflammatory response whether the inciting cause or agent is radiant, mechanical, chemical, infectious or immunological. Since the first recognition of the potent anti-inflammatory properties of these compounds in 1949, their therapeutic uses have increased dramatically. The unique biochemical, pharmacologic and physiologic properties of corticosteroids make them almost universally useful in the topical treatment of inflammatory conditions.

Corticosteroids are also useful in treating many conditions when used by systemic application. For example, their potent anti-inflammatory and immunosuppressive effects make them useful in the treatment of most rheumatic conditions and diseases.

While corticosteroids are highly effective in the treatment of the above systemic and local conditions, they suffer from one significant disadvantage. The size and shape of corticosteroids makes them exceedingly difficult to deliver percutaneously. Conventional and commercial topical steroid preparations are only marginally effective in delivering sufficient steroid for immediate treatment of local conditions; systemic steroid treatment by percutaneous delivery from known vehicles is unpredictable. Accordingly, a vehicle system which increases both the level and speed of penetration of the steroid through the skin would be more efficient in the treatment of localized conditions and, more importantly, would make systemic treatment by topical application viable. Effective systemic delivery of steroids by the topical mode of treatment is highly desirable since the topical treatment would result in a lower level of side effects than those associated with conventional (oral or parenteral) methods of administration when systemic steroid therapies are indicated.

The corticosteroid components useful in the present invention are well-known in the pharmaceutical art. They are described in detail in Miller and Munro, *Drugs*, 19, 119–134 (1980); and Wolfe, *Burger's Medicinal Chemistry*, 3, 4th Ed., John Wiley and Sons, New York, N.Y., pp. 1273–1316 (1981); both are incorporated herein by reference. The essential steroid structure consists of 17 carbon atoms, arranged in 4 rings, 3 six-membered rings and one 5-membered ring (See Base steroid structure, below). Since this is a rigid structure, small changes in the substituents can lead to significant changes in biological activity. This is presumably the result of a change in the interaction with specific site receptors involved in protein metabolism.

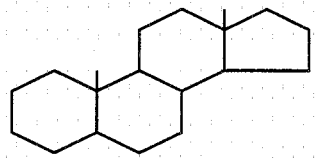

(BASE STEROID STRUCTURE)

Many valuable anti-inflammatory steroids have been developed by various modifications of the basic steroid structure. For example, the introduction of a double bond at the 1,2 position into hydrocortisone increases glucocorticoid activity by approximately 4 orders of magnitude while at the same time reducing mineralocorticoid effects. Prednisone and prednisolone are examples of such a modification.

Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate.

Mixtures of corticosteroids, particularly any of the above corticosteroids, are also useful in the present invention.

Examples of specific corticosteroids and their customary dosage levels useful in the present invention when local treatment is desirable can be broken down into four classes:

(1) Very potent

Beclomethasone dipropionate 0.5%
Clobetasol propionate 0.05%
Diflucortolone valerate 0.3%
Fluocinolone acetonide 0.2%

(2) Potent

Beclomethasone dipropionate 0.025%
Betamethasone benzoate 0.025%
Betamethasone dipropionate 0.05%
Betamethasone valerate 0.1%
Desonide 0.05%
Desoxymethasone 0.25%
Diflorasone diacetate 0.05%
Diflucortolone valerate 0.1%
Fluclorolone acetonide 0.025%
Fluosinolone acetonide 0.025%
Fluocinonide 0.05%
Flucortolone 0.5%

Fluprednidene (fluprednylidene) acetate 0.1%
Flurandrenolone 0.05%
Halcinonide 0.1%
Hydrocortisone butyrate 0.1%
Triamcinolone acetonide 0.1%

(3) Moderately Potent

Clobetasone butyrate 0.05%
Flumethasone pivalate 0.02%
Fluocinolone acetonide 0.01%
Flucortin butylester 0.75%
Flucortolone 0.2%
Flurandrenalone 0.0125%–0.025%
Hydrocortisone with urea 1%

(4) Mild

Dexamethasone 0.01%
Hydrocortisone (alcohol or acetate) 0.1%–1%
Methylprednisolone 0.25%

Particularly preferred corticosteroids for use in the present invention when topical treatment is desired include triamcinolone acetonide, hydrocortisone acetate, betamethasone valerate, fluocinolone acetonide, flupamesone, and mixtures of these compounds.

Examples of specific corticosteroids useful in the present invention when systemic treatment is desired include desoxycorticosterone, fludrocortisone, hydrocortisone, betamethasone, cortisone, dexamethasone, prednisolone, prednisone, methyl prednisolone, paramethasone, triamcinolone, and mixtures of these compounds.

Compositions of the present invention contain a safe and effective amount of the corticosteroid component; preferably the compositions contain from about 0.01% to about 10%, more preferably from about 0.02% to about 5%, of corticosteroid, by weight of the composition. The compositions most preferably contain about 0.05% to about 5% of corticosteroid, by weight of the composition. Of course, the level of steroid will vary with the steroid or steroids selected, the condition being treated, whether topical or systemic effects are desired, the surface area available for application, the particular vehicle selected, and the method of application. Higher levels are usually required when systemic effects are desired.

A second class of anti-inflammatory agents which are especially useful in the compositions of the present invention are the non-steroidal anti-inflammatory agents. The variety of compounds encompassed by this group are well-known to those skilled in the art. It is thought that these drugs act, at least in part, by the inhibition of prostaglandin synthetase. For detailed disclosure of the chemical structure, synthesis, side effects, etc., of non-steroidal anti-inflammatory agents, reference may be had to standard texts, including *Anti-inflammatory Agents, Chemistry and Pharmacology*, 1, R. A. Scherrer, et al., Academic Press, New York (1974), incorporated herein by reference.

Specific non-steroidal anti-inflammatory agents useful in the composition of the present invention include compounds of the the formula

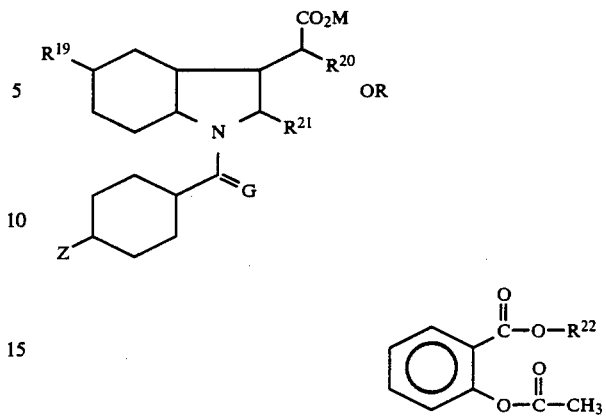

wherein $R^{19}$ is —$CH_3O$, (—$CH_3)_2N$, —F or —$CH_3$; $R^{20}$ and $R^{21}$ are —H or —$CH_3$, $R^{22}$ is —H, —$CH_3$, —$COOC_2H_5$, —$CH_2CHOHCH_2OH$, or —$CH_2OCOCH_3$, M is —H, alkali metal or $C_1$-$C_{20}$ alkyl, alkenyl, or aryl, Z is a halogen, $CF_3$ or $CH_3S$; and G is =O or (—H)$_2$. The foregoing include, without limitation, salicylic acid, acetyl salicylic acid, methyl salicylate, glycol salicylate, salicylmides, benzyl-2,5-diacetoxybenzoic acid, fulindac, ibuprofen, naproxen, ketoprofen, etofenamate, phenylbutazone, and indomethacin. Mixtures of these non-steroidal anti-inflammatory agents may also be employed, as well as the pharmaceutically-acceptable salts and esters of these agents. Piroxicam is also useful.

Non-steroidal anti-inflammatory agents are preferably present in the compositions of the present invention at levels of about 0.05% to about 10%, by weight of the composition. They are more preferably present at levels of about 0.25% to about 5%, and are most preferably present at levels of about 1% to about 5%, by weight of the composition.

Other analgesic, antipyretic and anti-inflammatory agents useful in the compositions of the present invention can be found in Goodman, et al., *The Pharmacological Basis of Therapeutics*, 5th Ed., pp. 325–358, Macmillan Publishing Company, New York, (1975); and Wolfe, *Burger's Medicinal Chemistry*, 3, 4th Ed., John Wiley and Sons, New York, N.Y., pp. 1273–1316 (1981); both are incorporated herein by reference.

Another class of compounds useful in the compositions of the present invention are compounds known generally as antimicrobial agents. The selection, clinical indications, structure, and side effects of such antimicrobial agents are well-known to the skilled artisan and can be readily determined by reference to any standard text, including Goodman, et. al., *The Pharmacological Basis of Therapeutics*, 5th Ed., pp. 1090–1247, Macmillan Publishing Company, New York, (1975), incorporated herein by reference.

Of the antimicrobials, a group of pharmaceutically-active agents especially suitable for topical administration in the compositions of the present invention are antibacterials, antibiotics, antifungals, and antivirals. Typical pharmaceutically-active agents in this category, useful in the compositions of the present invention, include, without limitation, sulfonomides, penicillins, cephalosporins, penicillinase, erythromycins, lincomycins, vancomycins, tetracyclines, chloramphenicols, streptomycins, and the like. Nonlimiting specific examples of the foregoing general groupings include erythromycin, erythromycin ethyl carbonate, erythromycin estolate, erythromycin ethylsuccinate, erythromycin lactobionate, lincomycin, clindamycin, tetracycline, chlortetracycline, demeclocycline, doxycycline, methacycline, oxytetracycline, minocycline, etc.

The antibacterials useful in the compositions and methods of the present invention include, without limitation, the chlorophors (chlorine releasing agents), phenols, substituted phenols, bisphenols, salicylanilides, hydroxy benzoic acids, polyhydric phenols, hydroxy quinolines, nitroheterocycles, e.g., nitrofurans and nitroimidazoles, nalidixic acid, oxolinic acid, quinoxaline- and phenazine-di-N-oxides, iodinin, cotrimoxazole, methenamine, B-lactam antibiotics such as the penicillins, cephalosporins, cephamycins, thienamycins, and clavulanic acid, nocardicins such as cephalothin and cefoxitin, non-lactam antibiotics such as the actinomycin group, bacitracin, tyrothricin, polymyxin and colistin, antibiotic polypeptides with a lactone ring such as etamycin and viridogrisein, staphylomycin, ostreogrycin, doricin, vernamycin, cycloheptamycin, telomycin, rufomycin A, ilamycin, streptogramime, mikamycin, gramicidin, albomycin, bacteriocin, the colicins, edeine, phytoactin, valinomycin, viomycin, the antimycins, distamycin A, neotropsin, thiostrepton, polyene antifungal antibiotics such as nystatin, pimaricin, lucensomycin, rimocidin, amphotericin B, primycin, levorins A and B, candidin, lagosin, filipin, chainim, mycoticin, and flavofungin, macrolide antibiotics such as methymycin, picromycin, lancamycin, oleandomycin, erythromycin, carbomycin, the spiramycins, chalcomycin, borrelidin, tylosin, angolamycin, nonactin, the oligomycins, and maridomycin, aminoglycoside antibiotics such as streptomycin, kanamycin, paromomycin, neomycin, and gentamicin, the tetracyclines, the steroidal antibiotics, the ansamycins such as rifamycin, the streptovaricins, and geldamycin, the glutarimids such as cycloheximide or actidione, naramycin B, antitumor E-73, the streptovitacins, nucleoside antibiotics such as puromycin, tubercidin, angustmycin and psicofurarine, cordycepin, blasticidin, gougerotin, the polyoxins, 3'-amino-3'-deoxyguanosine, nucleocidin, amicetin, sparsomycin; anthracycline antibiotics such as daunomycin, adriamycin, olivomycin, chromomycin and mithramycin, nogalamycin, leukaeomycin, steffimycin, carminomycin I, the phenazines, quinoxaline antibiotics such as echinomycin, the triostins, ionophores such as polyetherin A, monensin, and the nonclassifiable antibiotics such as actinomycetin, actithiazic acid, althiomycin, anthramycin, azaserine, the bleomycins, boromycin, bruneomycin, carzinophilin, cellocidin, chloramphenicol, cycloserine, flavensomycin, fumagillin, griseofulvin, hadacidin, kanchanomycin, lincomycin, micrococcin, the mitomycins, porfiromycin, nalidixic acid, novobiocin, pactamycin, patulin, pluramycin, protoanemonin, pyrrolnitrin, sarkomycin, sibiromycin, the sideromycins, tenuazonic acid, trichothecin, usnic acid, vancomycin and variotin.

Combinations of these agents are also particularly useful. For example, erythromycin or zinc erythromycin (See U.S. Pat. No. 4,261,982, Luedders, et al., issued Apr. 18, 1981, incorporated herein by refrence) in combination with clindomycin and tetracycline are especially useful, and preferred, for the treatment of acne. Other commonly employed antibacterial/antibiotic mixtures include the combination of polymycin-B, bacitracin and neomycin. Tetracycline or zinc erythromycin, used alone, are also preferred in the treatment of acne.

In dealing with non-acneiform, dermatological infections, penicillin and tetracycline are almost the universal drugs of first choice. Accordingly, penicillin, including synthetic penicillin and particularly the penicillinase-resistant varieties, or the use of tetracycline, form an especially preferred embodiment when used in the compositions of the present invention. Another agent which is especially preferred for systemic use, particularly in patients with sensitivity to penicillins, is erythromycin, including its common pharmaceutical salts and esters. Examples of common erythromycin esters would include erythromycin ethyl succinate, erythromycin lactobionate, erythromycin estolate, and the like.

Pharmaceutically-active fungistatic and fungicidal agents are useful in the compositions of the present invention. These include, without limitation, agents such as thiabendazole, chloroxine, amphotericin, candicidin, fungimycin, nystatin, griseofulvin, chlordantoin, clotrimazole, ethonam nitrate, miconazole nitrate, pyrrolnitrin, salicylic acid, fezatione, ticlatone, tolnaftate, tricetin, and zinc and sodium pyrithione. Other antifungals useful in the compositions and methods of the present invention include amphotericin B, 5-fluorocytosine, haloprogin, rifampin, pimaricin, heavy metals such as $Ag^+$, $Hg^{+2}$, $Cu^{+2}$, and $Zn^{+2}$, chelating agents such as substituted biguanidines, triphenylmethane dyes, and EDTA, phenolics such as phenol, cresol, m-cresyl acetate, benzoic acid, and p-hydroxybenzoic acid, salicylanilide, 5-chlorosalicylamlide, 5,5'-dibromosalicil, 3,5-dibromosalicylaldehyde, ethyl vanillate, sulfur-containing antifungals molecules such as the dithiocarbamates and imidazoles, pyrimidines such as 2,4-dichloro-B(2,4-dichlorobenzyloxyphenethyl)imidazole, (as well as miconazole and 5-fluorocytosine recited above), sulfonamides, and sulfones such as sulfaclomide and sulfa-1-ethylcytosine.

Antifungal agents particularly useful in the compositions of the present invention include nystatin, amphotericin-B, griseofulvin, tolnaftate, and mixtures of these antifungals.

Antiviral agents useful in the compositions of the present invention include, without limitation, idoxuridine, iododeoxyuridine, amantadine, methisazone, cytarabine, and mixtures thereof.

A class of antiviral agents particularly useful in compositions of the present invention are 6- or 2,6-substituted purine antiviral actives, such as 9-(2-hydroxyethoxymethyl)guanine. The method of preparing these compounds, and their uses and clinical indications as antivirals, are well-known to those skilled in the art. See U.S. Pat. No. 4,199,475, Schaeffer, issued Apr. 22, 1980; U.S. Pat. No. 4,146,715, Schaeffer, issued Mar. 27, 1979; and European Patent Application No. 44,543, published Jan. 27, 1982, all of which are incorporated herein by reference. See also U.S. patent application Ser. No. 383,891, filed June 1, 1982, Copper, also incorporated herein by reference.

Preferred 6- or 2,6-substituted purine antiviral compounds useful in this invention are of the formula

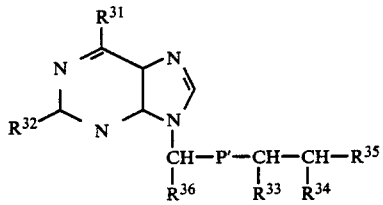

wherein P' is sulfur or oxygen, $R^{31}$ is hydrogen, a halogen, hydroxy, alkoxy, azide, thio, alkylthio, amino, alkylamino or dialkylamino; $R^{32}$ is hydrogen, a halogen, alkylthio, acylamino, amino or azide; $R^{33}$ is hydrogen, a straight, branched or cyclic alkyl, hydroxyalkyl benzyloxyalkyl or phenyl; $R^{34}$ is hydrogen, hydroxy or alkyl; $R^{35}$ is hydrogen, hydroxy, amino, alkyl, hydroxyalkyl, benzyloxy, benzoyloxy, benzoyloxymethyl, sulfamoyloxy, phosphate carboxypropionyloxy, straight chain or cyclic acyloxyl having from 1 to 8 carbon atoms, or substituted carbamoyl group having the formula NHCO—Q; wherein Q is alkyl, aryl, or aralkyl optionally substituted by one or more substituents selected from sulfonyl, amino, carbamoyl or hydrogen; $R^{36}$ is hydrogen or an alkyl, provided that when P' is oxygen and $R^{32}$, $R^{33}$, $R^{34}$ and $R^{36}$ are H, $R^{31}$ is not amino or methylamino when $R^{35}$ is hydrogen or hyroxy. Pharmaceutically-acceptable organic and inorganic acid salts of the above, such as the salt of latic, acetic, malic, hydrochloric or sulfuric acids, may also be employed. The reaction product of the above with zinc or zinc salts may also be employed.

Preferred antiviral compounds of the invention are of the formula above, wherein P' is sulfur or oxygen, $R^{31}$ is hydroxy, $R^{32}$ is amino, $R^{33}$ is hydrogen, a straight or branched chain or cyclic alkyl, hydroxyalkyl, benzyloxyalkyl or phenyl, $R^{34}$ is hydrogen, hydroxy or lower alkyl, $R^{35}$ is hydrogen, hydroxy amino, alkyl, hydroxyalkyl, benzoyloxy, benzoyloxy alkyl, benzyloxy, sulfamoyloxy, phosphate, carboxypropionyloxy, or acetoxy, $R^{36}$ is hydrogen, alkyl or hydroxyalkyl, or a pharmaceutically-acceptable salt of the above.

Highly preferred antiviral compounds of this invention include 9-(2-hydroxyethoxymethyl)guanine, 2-amino-9-(2-hydroxyethoxymethyl)adenine, and pharmaceutically-acceptable salts, and esters of these compounds. Especially preferred are 9-(2-hydroxyethoxymethyl)guanine, as well as its pharmaceutically-acceptable salts and esters.

The compositions of this invention typically contain from about 0.01 to about 10%, by weight of the composition, of the substituted purine antiviral, and preferably contain about 0.05% to about 5%. The substituted purine antiviral is most preferably present at a level of from about 0.5% to about 5%, by weight of the composition.

Other antivirals useful in the compositions and methods of the present invention include 1-methylisatin-3-thiosemicarbazone(methisazone), 5-trifluoromethyl-2'-deoxyuridine(triflurothymidine), amantadine HCl, rimantadine HCl, tromantadine HCl and other amantane-amines and related compounds, vidarabine, cytarabine, ribavirin, inosiplex, levamisole, bonaphton, tebrophen, florenal, the thiosemicarbazones such as methisazone (recited above), the benzimidazoles such as 2-(α-hyroxybenzyl)benzimidazole, the ureas and thioureas such as 1-(benzothiazol-2-yl)-3-substituted ureas, the guanidines and biguanides, pyrimidine nucleosides and nucleotides including the 5'-amino-2',5'-dideoxypyrimidine nucleosides, bisbasic substituted polycyclic aromatic antivirals such as tilorone HCl, phosphonoacetic acid, the decalin (trans form) derivatives, calcium elenolate, the flavones including quercetin, the rifamycins, the streptovaricins, gliotoxin and its analogues, distamycin A and its analogues, 9-methylstreptimidon, the bleomycins including bleomycin A2, and glucose derivatives such as N-fluoroacetylglucosamine and 2-deoxy-D-glucose.

Also useful in the compositions of the present invention are the antivirals described in U.S. Pat. No. 4,027,023, Schaeffer, issued May 31, 1977; U.S. Pat. No. 4,060,616, Schaeffer, issued Nov. 29, 1977; U.S. Pat. No. 4,287,188, Schaeffer, issued Sept. 1, 1981; U.S. Pat. No. 4,294,831, Schaeffer, issued Oct. 13, 1981; U.S. Pat. No. 4,323,573, Schaeffer, issued Apr. 6, 1982; U.S. Pat. No. 4,360,522, Schaeffer, issued Nov. 23, 1982; U.S. Pat. No. 4,199,574, Schaeffer, issued Apr. 22, 1980; U.S. Pat. No. 4,146,715, Schaeffer, issued Mar. 27, 1979; U.S. Pat. No. 3,956,277, Elion, issued May 11, 1976; and U.S. Pat. No. 4,038,479, Elion, issued July 26, 1977; all of the above are hereby expressly incorporated by reference.

Analgesics useful in the compositions and methods of the present invention include morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol and nefopam.

Another group of analgesics useful in the compositions and methods of the present invention are capsaicin(8-methyl-N-vanillyl-6E-nonenamide), "synthetic" capsaicin(N-vanillylnonamide), and related compounds. The use, synthesis, formulation, etc., of these compounds may be found in U.S. Pat. No. 4,313,958, LaHann, issued Feb. 2, 1982; U.S. Pat. No. 4,238,505, Nelson, issued Dec. 9, 1980; U.S. patent application Ser. No. 359,464, LaHann, et al., filed Mar. 18, 1982; U.S. patent application Ser. No. 360,953, Buckwalter, et al., filed Mar. 23, 1982; U.S. patent application Ser. No. 381,672, Buckwalter, et al., filed May 25, 1982; and U.S. patent application Ser. No. 384,685, Buckwalter, et al., filed June 3, 1982. All of the above are expressly incorporated herein by reference.

The antiarthritics useful in the compositions of the present invention include, without limitation, the steroid and nonsteroidal anti-inflammatories discussed above, the bone active agents discussed herein, and gold salts.

Antitussives useful in the compositions and methods of the present invention include ephedrine, phenylpropanolamine, theophylline, codeine, pholcodine, hydrocodone, noscapine, dextromethorphan, levopropoxyphene, carbetapentane, pipazethate, isoaminile, chlorphendianol, benzonatate, dimemorphan and zipeprol.

The sedatives, hypnotics, barbiturates, and the like useful in the compositions and methods of the present invention include amobarbital, aprobarbital, barbital, hexobarbital, mephobarbital, methohexital, pentobarbital, phenobarbital, probarbital, secobarbital, talbutal, thiamylal, thiopental, chlorodesmethyldiazepam, estazolam, flunitrazepam, flurazepam, fosazepam, lorazempam, nimetazepam, nitrazepam, nordiazepam, quazepam, triazolam, pyrithyldione, iminophenimide, ethinazone, mecloqualone, methaqualone, clomethiazole, fenadiazole, ethinamate, hexapropymate, meprobamate, oxanamide, valnoctamide, butesamide, diethylallylacetamide, trimethobenzglycine, ibrotamide, capuride, ectylurea, apronalide, bromvalurea, acetylcarbromal, carbromal, amylene hydrate, chloretone, methylpentynol, brommethylpentynol, ethchlorvynol, methylphenylbutyndiol, paraldehyde, and choral hydrate and its derivatives.

The antianxiety agents useful in the compositions and methods of the present invention include meprobamate, tybamate, phenprobamate, emylcamate, chlormezanone, nordiazepam, nitrazepam, diazepam, oxazepam, hemisuccinate, temazepam, camazepam, lorazepam, clonazepam, bromazepam, prazepam, flurazepam, chlordiazepoxide, demoxepam, clorazepate dipotassium, medazepam, and triazolam.

The cardiac drugs useful in the compositions and methods of the present invention include verapamil, quinidine, digitoxin, $\beta$-methyldigoxin, digoxin, lanatoside C, lanthanum, lidocaine, propranolol, phenytoin, disopyramide, quinidine, procaine, procainamide, practolol, bretylium tosylate, aprindine, mexiletine, diphenidol, propafenone, tocainide, quat and steroid antiarrhythmics, antianginal agents such as sodium nitrate, amyl nitrite, nitroglycerin, erythritol tetranitrate, pentaerythritol tetranitrate, mannitol hexanitrate, isosorbide dinitrate, trolnitrate phosphate, phentolamine, tolazoline, sodium nitroprusside, prazosin, hydralazine, and calcium channel blockers such as varapamil HCl, diltiazem HCl, and nifedipine.

Antihypertensive agents useful in the compositions and methods of the present invention include, without limitation, $\beta$-blocking agents, diuretics, central adrenergic agents and vasodialators. These include clonidine, flutonidine, tolonidine, naphazoline, tetrahydrozoline, triamenidine, xylazine, guanabenz, $\alpha$-methyldopa, metaraminol, methyloctapamine, dopamine-$\beta$-hydroxylase, monamine oxidase inhibitors, ganglionic blockers, reserpines, adrenergic neurone blockers such as guanethidine sulfate, bethanidine, guanoxan, guanadrel, guanachlor, aminoethylguanines, debrisoquin and bretylium, -adrenergic receptor-blocking agents such as phentolamine, tolazoline and phenoxybenzamine (for permanent blocking), prazosin, indoramine, nicergoline and methyl-apogalanthamine, $\beta$-adrenergic receptor-blocking agents such as the arylethanolamines and aryloxypropanolamines, e.g., propranolol, pindolol, alprenolol, oxprenolol, bunitrolol, tolamolol, practolol, atenolol, metoprolol, acebutolol, nadolol, timolol, and sotalol. Direct acting vasodialators including sodium nitroprussie, diazoxide, hydralazine, minoxildil, and dihydropyridines are useful.

Among the diuretics and uricosuric agents useful in the compositions of the present invention are hydrochlorothiazides and other thiazides, bendroflumethiazide, benzthiazide, buthiazide, chlorothiazide, cyclopenthiazide, cyclothiazide, hydrochlorothiazide, hydroflumethiazide, methyclothiazide, polythiazide, trichlormethiazide, alipamide, chlorthalidone, clopamide, clorexolone, diapamide, mefruside, metolazone, and quinethazone, potassium sparing and thiazide combinations, (i.e., a thiazide or hydrochlorothiazide+-spironolactone, triamterelene, clazolimine, or amiloride), chlorthalidones, 1-oxoisoindolines, high ceiling diuretics such as ethacrynic acid, bumetanide, furosemide, indapamide, xipamide, piretanide, triflocin, muzolimine, 2-aminomethyl-3,4,6-trichlorophenol, etozolin, steroidal aldosterone antagonists including spironolactone, potassium canrenoate, potassium prorenoate, and potassium mexrenoate, aldosterone inhibitors including metyrapone, cyclic polynitrogen compounds including xanthines, aminouracils, triazines such as 1-allyl-3-ethyl-6-aminouracil, amiloride, aminometradine, amisometradine, chlorazanil, clazolimine, aminophylline, triamterene, and the triazines. The uricosuric or uricosuric-diuretic agents useful herein include probenecid, sulfinpyrazone, allopurinol, salicyclic acid and tienilic acid.

The drugs for neoplastic diseases useful in the compositions and methods of the present invention include the antimetabolites such as glutamine, folic acid, pyrimidine, and purine antagonists, ribonucleoside diphosphonate and reductase inhibitors, nitrogen mustards, aziridines, methanesulfonic esters, 1,2-epoxides, nitrosoureas, triazenolimidazoles, procarbazine, mitotic inhibitors, hormones, L-asparaginase, mexthotrexate-5-flouro-uracil, hexamethylmelamine, cis-dichlorodiamineplatinum (II), and DNA complexing agents such as the actinomycins, mithramycins, bleomycins and anthracyclines.

Local anesthetics useful in the compositions and methods of the present invention include benzocaine, lidocaine, ketocaine, chloroprocaine, procaine, ambucaine, propoxycaine, etidocaine, mepivacaine, prilocaine, quatracaine, tetracaine, tolcaine, aptocaine and bupivacaine. STX, TTX, and the like, (agents which cause a reversible blocking of nerve conduction) are also useful.

Anorexigenics useful herein include phenythylamine derivatives including amphetamine, dextroamphetamine, methamphetamine, benzphetamine, fenfluramine, chlorphentermine, chlortermine, phentermine, diethylpropion, phenylpropanolamine, 1-methyl-2-phenylmorpholine, phendimetrazine, and phenmetrazine, mazindol, oxazolines, thioimidazolines, phenoxyalkyleneamines, biguanides, and L-histidine.

The bone-active organophosphonate compounds useful in the compositions and methods of the present invention are those that find particular utility in the treatment and therapy of irregular or anomalous mobilization and deposition of calcium phosphate salts (bone mineral) in humans or other animals. They are also disclosed as being useful in the treatment of arthritis. See U.S. Pat. No. 3,683,080, Francis, issued Aug. 8, 1972; U.S. Pat. No. 4,234,645, Gunther, et al., issued Nov. 18, 1980, and U.S. Pat. No. 4,216,212, Flora, et al., issued Aug. 5, 1980; all of which are incorporated herein by reference. The organophosphonate compounds particularly useful in the compositions of the present invention include dichloromethanediphosphonic acid, ethane-1-hydroxy-1,1-diphosphonic acid, methane diphosphonic acid, the pharmaceutically-acceptable salts of these acids, and mitures thereof.

OPTIONAL COMPONENTS

In addition to the components described above, the compositions of this invention may optionally contain a cosmetically acceptable solvent. The solvent, if used, should not significantly interfere with the penetration action of the binary combination, and should preferably evaporate rapidly and completely to leave only the active components of the composition at the site of application. Preferred solvents include ethanol and isopropanol.

Water may be used as a solvent or component in the compositions of the present invention. However, simple addition of water to these compositions may cause some or all of the penetration-enhancing compounds to precipitate out. Such action in the formulation of the compositions of the present invention may significantly reduce the overall effectiveness of the system. In order to prevent this, if water is used, it is preferred that an emulsion or gel be formed. Since these compounds themselves, used alone, do not form an emulsion or gel stable enough for the intended use of the compositions, emulgents or gelling agent should therefore be employed.

Such solvents, i.e., water, ethanol or 2-propanol (isopropanol; isopropyl alcohol), may comprise from 0% to about 80% of the total composition by weight. Ethanol and 2-propanol are preferably present at a level of 0% to about 70%.

However, certain other solvents, cosolvents, excipients, lipid materials and certain other components conventionally found and generally acceptable in topical pharmaceutical compositions must be carefully evaluated or, in the alternative, avoided in the practice of the present invention to achieve maximum enhanced penetration. It is thought that such compounds compete for the role the vehicle components of the present invention play, or the site these components occupy, in assisting the active in penetrating the stratum corneum. This competition prevents or retards the penetration of the stratum corneum by the active or actives. Some of these compounds may also compete with the lipids of the stratum corneum for the penetration-enhancing compounds, causing these compounds to preferentially partition into such lipid-like compounds in the vehicle rather than the lipids of the stratum corneum. Thus, such compounds must be evaluated for such activity or, if such an evaluation is impractical, they should be avoided when formulating the compositions of the present invention. Maximum penetration is thus more likely to be realized. If used, such compounds should generally be used at the lowest level at which they serve their intended formulation function, far below art-established levels when feasible. However, it will be appreciated that such compounds may be tolerated when absolutely necessary to achieve cosmetic acceptability.

For example, hydrocarbons such as liquid petrolatum (mineral oil, liquid paraffin, paraffin oil), white petrolatum, yellow petrolatum, paraffin, microcrystalline wax, and ceresin are all known to be useful as hydrophobic vehicles or structural matrix formers in topical pharmaceutical formulations. However, all of these excipients are capable of significantly interfering with the penetration enhancing abilities of certain embodiments of the present invention. It is thought that these compounds inhibit the ability of the penetration-enhancing vehicle components to effectively disrupt the intercellular lipid structure of stratum corneum by perhaps preventing the penetration-enhancing vehicle components from effectively reaching the lipids of the stratum corneum. While a certain level of such ingredients can be tolerated in a system which is otherwise particularly effective, in a preferred embodiment of the present invention the level of any single such ingredient is limited to less than about 10%, and preferably less than about 5%, by weight of the composition.

Certain straight chain, saturated $C_{16}-C_{20}$ normal fatty alcohols may also interfere with penetration and should also be avoided if such interference is too great. Cetyl alcohol and stearyl alcohol are extremely common, ubiquitous ingredients in topical formulations. Both of these alcohols are capable of significant interference with the penetration enhancement of the present vehicle. These alcohols, as well as the straight chain saturated $C_{18}$ normal alcohol, are extremely likely to interfere with the systems of the present invention. Accordingly, in a preferred embodiment, the compositions of the present invention are substantially free of such compounds, i.e., the level of any single such compound is less than 3.5%, by weight of the composition, and more preferably the level is less than 1%. In a highly preferred embodiment the compositions of the present invention contain less than 0.5%, by weight of the composition, of any single member of said alcohols.

Certain fatty acids are also capable of gross interference with penetration-enhancement. These acids include the straight chain $C_4-C_{20}$ saturated monocarboxylic and dicarboxylic acids. Octanoic and decanoic acid are also particularly likely to interfere in the systems of the present invention. In a preferred embodiment, the compositions of the present invention are substantially free of these acids, i.e., contain less than about 3.5%, by weight of the composition, of any single member of straight chain $C_4-C_{20}$ saturated monocarboxylic and dicarboxylic acids, and more preferably less than about 1% of said acids. In a highly preferred embodiment the compositions of the present invention contain less than 0.5%, by weight of the composition, of any single member of said acids.

The compositions of the present invention may additionally contain other adjunct components conventionally found in pharmaceutical compostions, not recited above, at their art-established usage levels. Thus, for example, the compositions may contain two or more compatible phrarmaceutically-active materials for combination therapy; antimicrobials, antipruritics, astringents, local anesthetics, or non-steroidal anti-inflammatory agents could be employed when the active initially selected for therapy is a steroid. They may also contain materials useful in physically formulating various dosage forms of the present invention, such as excipients, dyes, perfumes, fragrances, opacifiers, thickening agents, preservatives, anti-oxidants, gelling agents, surfactants and stabilizers. Such materials, when added, should not unduly interfere with the penetration enhancement of these compositions. Such formula modifications to improve cosmetic acceptability are well within the skill of workers in the cosmetic and dermatological arts and, by themselves, constitute no part of the present invention.

All optional components should be selected to prevent substantial interference with the penetration ability of the composition. In determining the degree of penetration retardation or interference a particular agent causes, simply take the desired formulation and compare it cosmetically with a formulation which does not contain the suspect ingredient, or which contains the ingredient at a lower level. The same formulations should then be compared for efficacy using the method described for Examples 2-31. If the desired formula is cosmetically acceptable and also capable of delivering the desired/necessary level of active, it will be appreciated that no problem exists. However, if a composition or formula is cosmetically acceptable, but incapable of delivering the desired/necessary level of active, the penetration-interfering ingredient should be gradually reduced, or a different formulation or embodiment selected and tested, until the formulation with the highest degree of cosmetic acceptability capable of delivering the necessary/desired level of active is found.

It can be seen from the foregoing that the compositions of the present invention admit of considerable variation, so long as the critical components of 1-dodecylazacycloheptan-2-one, and a diol compound or a second N-substituted azacycloalkyl-2-one compound is present, within the ranges and ratios indicated above.

METHOD OF USE

It will be appreciated that this invention provides a method for treating and preventing conditions, or the risks, pain or other pathologies associated with such conditions which respond to the activity of the active or actives selected for incorporation into the 1-dodecylazacycloheptan-2-one vehicle. Such conditions may be responsive to either the local or systemic activity of the selected active. When local treatment is desired, the compositions of the present invention are applied to the afflicted situs. When systemic treatment is desired, the compositions of the present invention are applied to an application situs, preferably from a sustained release film, web, bandage or device. Such devices are well-known in the art, and examples of such films, webs, bandages, devices, and the like can be found in Johnson, J. C., et al., *Sustained Release Medications, Chemical Technology Review* No. 177, Noyes Data Corporation, Park Ridge, N.J., pp. 82–113, (1980), incorporated herein by reference. When both local and systemic treatments are indicated or desired, the compositions of the present invention can be applied at the afflicted situs, an application situs, or both.

While the choice of any particular agent in the treatment of a specific condition may be dictated by such factors as cost, availability, safety, and the like, such a choice frequently represents the personal experience of the artisan which may or may not be reproduceable. Further, the availability of many actives with equivalent efficacy makes the choice of the "best" specific agent or active, or combination or agents or actives, difficult. However, the selection of an agent, or combination of agents, which can be effectively penetrated to manage any foreseeable condition is well within the skill of the art, and the actual selection of such agents (other than the selection of a penetrable agent or active) plays no part of this invention. For example, when a steroid is incorporated into the compositions of the present invention and the resulting composition is applied to an afflicted/application situs, this invention provides a method for treating and preventing nonendocrine immunologic or rheumatic diseases, such as rheumatoid arthritis, rheumatic fever, disseminated lupus erythematosus, hypersensitivity reactions, such as bronchial asthma, serum sickness, anaphylaxis, bee stings, angioneurotic edema, hay fever, hemolytic enemia, drug reactions and agranulcytosis. Incorporation of a steroid into the compositions of the present invention and application of the resulting composition to an application situs also provides a method for treating diseases of the liver such as chronic active hepatitis, as well as certain neurological conditions, such as cerebral edema or an increase in intracranial pressure. The incorporation of a steroid and application of the resulting composition to an application situs further provides a method for treating and preventing inflammatory conditions such as ulcerative colitis, dermatitis (atopic, eczematoid, exfoliative, stasis, nummular, contact, or seborrheic), pemfhigus, gout and other inflammations of skin or mucous membranes caused by chemical, thermal, mechanical or radiant agents. In addition, the present invention may be formulated and used with a steroid in a veterinary context, for example in the treatment of dermatological disorders characterized by inflammation and dry or exudative dermatitis, eczematous dermatitis, contact dermatitis, seborrheic dermatitis, and as an adjunct in the treatment of dermatitis due to parasitic infestation.

It will be appreciated that the number and severity of side effects produced by systemic corticosteroid therapy are significantly increased when compared with localized therapy. Thus, the decision to use corticosteroids for systemic treatment requires a clear definition of the benefits to be gained by such treatment, an identification of the risks the subject may encounter, so that informed overall assessment may be made. The risks attendant the systemic use of corticosteroids include abnormal sodium reabsorption and potassium excretion. This interference with the two important monovalent ions may result in hypokalemic alkalosis, edema, hypertension and other abnormalities associated with electrolyte imbalances. Corticosteroids, when delivered systemically, may also suppress the natural healing process of injuries, especially those that cause a break in the integument. The immunosuppresive properties of corticosteroids, the very property which makes them valuable in the treatment of immunologically mediated disease, can result in a compromise of the subject's ability to fight infection. They can also mask the symptoms of some infections, thus preventing or delaying diagnosis and treatment. Further side effects include abnormal function within the gastrointestinal, cardiovascular, endocrine and central nervous systems. These may occur in any subject receiving a supraphysiologic concentration of corticosteroid hormones or their synthetic equivalents. In general, the frequency and severity of such side effects are proportional to the dose given, and the duration of treatment. When either the amount per dose, or the period of time over which therapy is given is increased, an increase in side effects can also be anticipated.

Accordingly, in actual clinical practice, two rules become paramount when systemic corticosteroid therapy is to be administered in the treatment of any condition or episode:

(1) the period of administration must be as short as possible; and (2) the delivered dosage must be the smallest one that will achieve the desired effect.

When the therapy which calls for single administration is indicated, the single administration can be viewed as inocuous in character. Short courses of systemic steroid therapy of substantial doses may be proper in conditions which are not life-threatening assuming the absence of specific contraindications. However, it is generally accepted that courses of long-term therapy at a high dosage should be reserved only for life-threatening disease. This rule is occassionally violated justifiably when the patient is threatened with significant and permanent disability. See Goodman and Gilman, *The Pharmacological Basis of Therapeutics,* Macmillan Publishing Company, Inc., pp. 1497–1500 (1975), incorporated herein by reference.

In summary, the individual dosage must be particularly suited to the individual condition being treated when using the compositions of the present invention for systemic treatment as well as localized treatment when systemic effects are possible side-effects of such localized treatment.

When antimicrobials (including the sulfonomides, penicillins, cephalosporins, penicillinase, erythromycins, lincomycins, vancomycins, tetracyclines, chloramphenicols, streptomycins, etc.) are incorporated within the compositions of the present invention, they provide a method of treating infections, including abscesses, bacteremia, endocarditis, pneumonia, meningitis, osteomyelitis, pharyngitis, scarlet fever, otitis media, sinusitis, cellulitis, erysipelas, dental infections, subacute endocarditis, urinary tract infections, genital infections, hepatic disease, wound infections, recurrent abortion, erysipeloid, "malignant postule", gas gangrene, tetanus, biliary tract infections, typhoid fever, acute gastroenteritis (caused by Salmonella or Shigella), opportunistic infections (i.e., infections in patients undergoing recurring immunosuppressive therapies), epiglottitis, laryngotracheobronchitis, chancroids, glanders, syphilis, yaws, relapsing fever, cervicofacial, abdominal, theracic and other lesions, "atypical" viral pneumonia, nonspecific urethritis, pelvic abscesses, septicemia, skin and superficial mucous membrane lesions (generally caused by *Candida albicans*), bone lesions, skin, hair and nail infections, sporotrichosis, keraboconjunctivitis, influenza and herpes, by applying the composition to the afflicted situs or to an application situs, as appropriate.

More specifically, in a preferred embodiment, a safe and effective amount of a pharmaceutically-active antiviral agent selected from the group consisting of idoxuridine, iodoueoxyuridine, or a 6- or 2,6-substituted purine, recited above, is incorporated into the compositions of the present invention and applied to the afflicted situs, and a method of treating the pain and inflammation associated with herpes simplex, herpes zoster, and herpes varicella infection, including labial and genital herpes, is provided. Another preferred embodiment encompasses incorporating a safe and effective amount of griseofulvin into the compositions of the present invention and a method of treating the pain and inflammation associated with infections of skin, hair or nails, is accordingly provided when the resulting composition is topically applied to the afflicted situs.

The compositions of this invention are typically applied one to six times daily to the afflicted situs when topical treatment is desired. When systemic effects are also desired, or when it is desired to reduce the chance of the spread of infection, the compositions of this invention are applied to larger areas, more frequently, or from a mechanical sustained release device or dressing.

Topical treatment regimens according to the practice of this invention comprise applying the compositions herein directly to the skin, i.e., at the afflicted situs or the application situs. The compositions may also be formulated for use in the oral or vaginal cavities. The rate of application and duration of treatment will, of course, depend on many factors. A typical safe and effective usage rate for topical localized treatment is about 1 mg of the total topical composition per square centimeter of skin to about 10 mg of total topical composition per square centimeter of skin per application and about 1 mg of the total topical composition to about 100 mg of the total topical composition per square centimeter of skin when systemic, or local and systemic, effects or treatment are desired. The skilled artisan will appreciate that this application rate will vary with the desired effect (systemic, local, or systemic and local), the condition being treated, its progress and response, the area involved, the severity and nature of the condition being treated, the nature of the actives or carriers, the presence or absence of penetration-interfering solvnts, cosolvents, excipients and lipids, the physical condition of the patient, concurrent therapies being administered, the concentration of the actives or carriers being used, as well as other factors within the particular knowledge of the patient and/or physician within the scope of sound medical judgment. However, usage rates of up to 500 mg of total composition per square centimeter of skin may be used when the composition is used as an occlusive dressing. Even larger rates may be employed when a mechanical sustained delivery device or dressing is used.

The compositions can be applied once every twenty-four hours to about twenty-four times every twenty-four hours. Application intervals of every 4 hours to every 12 hours are preferred. A treatment regimen of application every 6 hours is particularly preferred because it minimizes the amount of the selected pharmaceutically-active agent which is applied at one time while reducing the inconvenience of frequent applications. However, any treatment regimen which allows a safe and effective amount of the selected pharmaceutically-active agent to reach the afflicted situs or the bloodstream can be employed while using the compositions of this invention. For possibly compatible and related topical compositions and treatment regimens, see co-pending U.S. patent applications entitled "Improved Penetrating Topical Pharmaceutical Compositions Containing Corticosteroids" Cooper, et al., Ser. No. 576,065, filed Feb. 1, 1984; and "Penetrating Topical Pharmaceutical Compositions Containing N-(2-Hydroxyethyl)pyrrolidone", Cooper, Ser. No. 506,273, filed June 21, 1983; both expressly incorporated herein by reference.

The following are nonlimiting examples of the composition of the present invention. They are formulated by conventional methods by simply mixing all components thoroughly.

EXAMPLE 1

Part A

| Composition I | |
|---|---|
| Triamcinolone acetonide (Triamcinolone hereafter) | 1.0% |
| Propylene Glycol (1,2-propanediol) | 95.0% |
| 1-dodecylazacycloheptan-2-one | 4.0% |
| Composition II | |
| Hydrocortisone acetate | 1.0% |
| Propylene Glycol (1,2-propanediol) | 94.0% |
| 1-dodecylazacycloheptan-2-one | 5.0% |
| Composition III | |
| Betamethasone valerate | 0.5% |
| Propylene Glycol (1,2-propanediol) | 93.5% |
| 1-dodecylazacycloheptan-2-one | 6.0% |
| Composition IV | |
| Fluocinolone acetonide | 0.5% |
| Propylene Glycol (1,2-propanediol) | 94.5% |
| 1-dodecylazacycloheptan-2-one | 5.0% |
| Composition V | |
| Flupamesone | 0.5% |
| Propylene Glycol (1,2-propanediol) | 97.5% |
| 1-dodecylazacycloheptan-2-one | 2.0% |
| Composition VI | |
| Triamcinolone | 0.5% |
| 1,2-butanediol | 95.5% |
| 1-dodecylazacycloheptan-2-one | 4.0% |
| Composition VII | |

-continued

| | |
|---|---|
| Indomethacin | 0.5% |
| 1,3-butanediol | 97.5% |
| 1-dodecylazacycloheptan-2-one | 2.0% |
| Composition VIII | |
| phenylbutazone | 1.0% |
| 1,2-butanediol | 97.0% |
| 1-dodecylazacycloheptan-2-one | 2.0% |
| Composition IX | |
| methyl salicylate | 2.0% |
| 1,3-butanediol | 93.0% |
| 1-dodecylazacycloheptan-2-one | 5.0% |
| Composition X | |
| Betamethasone valerate | 2.0% |
| 1-(2-hydroxyethyl)-azacyclopentan-2-one | 93.0% |
| 1-dodecylazacycloheptan-2-one | 5.0% |
| Composition XI | |
| Fluocinolone acetonide | 5.0% |
| 1-ethylazacycloheptan-2-one | 92.0% |
| 1-dodecylazacycloheptan-2-one | 3.0% |
| Composition XII | |
| Flupamesone | 1.0% |
| Hydrocortisone Acetate | 1.0% |
| Propylene glycol (1,2-propanediol) | 93.0% |
| 1-dodecylazacycloheptan-2-one | 5.0% |
| Composition XIII | |
| Desoxycorticosterone | 5.0% |
| 2-pyrrolidone | 90.0% |
| 1-dodecylazacycloheptan-2-one | 5.0% |
| Composition XIV | |
| Prednisolone | 5.0% |
| Propylene Glycol (1,2-propanediol) | 51.0% |
| 2-pyrrolidone | 40.0 |
| 1-dodecylazacycloheptan-2-one | 4.0% |
| Composition XV | |
| Prednisone | 2.0% |
| 1,2-butanediol | 54.0% |
| 1-(2-hydroxyethyl)azacyclopentan-2-one | 40.0 |
| 1-dodecylazacycloheptan-2-one | 4.0% |
| Composition XVI | |
| 9-(2-hydroxyethoxymethyl)guanine | 5.0% |
| 1,2 propanediol | 90.0% |
| 1-dodecylazacycloheptan-2-one | 5.0% |

The following are nonlimiting examples of the methods of the present invention.

EXAMPLE 1

Part B

Composition I is applied to a human afflicted with dermatitis at the afflicted situs at a rate of 5 mg of composition per square centimeter of skin three times daily for a period of 5 days. Complete elimination of inflammation is noted after 48 hours. Substantially similar results are obtained when the composition is replaced by Compositions II, III, IV or V of Example 1.

EXAMPLE 1

Part C

Composition XVI is applied to a human afflicted with a herpetic lesion at the afflicted situs at a rate of 2 mg of composition per square centimeter of skin six times daily for a period of 2 weeks. Reduction in the size of the lesion is noted after 3 days.

PENETRATION STUDIES

The following Penetration Studies demonstrate the penetration-enhancing capabilities of the compositions and methods of the present invention. These nonlimiting Examples demonstrate the ability possessed by the formulations of the present invention to additionally enhance the penetration of a pharmaceutically-active agent (here Triamcinolone) from a vehicle containing Azone. When Azone is used in the binary combinations of the present invention, and the diol compounds, cyclketo compounds or mixtures thereof are used at their critical levels, penetration is greatly enhanced when contrasted with compositions which contain either of these elements alone, or which contain either or both elements but at levels below the critical level recited herein.

The following Penetration Studies carried out in the following manner. Human skin (heat-separated or dermatomed abdominal epidermis, taken at autopsy, or excised, full thickness hairless mouse skin) is placed in a standard Franz diffusion apparatus (Crown Glass Company, Somerville, NJ) in a horizontal position between a lower, capped diffusion cell and an upper, open cell. A normal saline solution is added to the lower diffusion cell, abutting the subcutaneous side of the skin. The test composition (comprising a solution of active or actives added to the carrier at the indicated formulation in a conventional manner by thoroughly mixing) is added to the diffusion cell abutting the epidermal side of the skin.

This cell assembly is kept at a constant temperature of about 31° C. At appropriate or desired intervals (these are the time designations given in the following examples) each diffusion cell assembly is opened and the diffusate from the cell abutting the subcutaneous side of the skin is withdrawn. Drug actives in a diffusate is measured using standard analytical techniques. Each trial is run on a separate sample of skin.

In the following Examples, (*) indicates that human skin was selected for this trial, and (**) indicate that hairless mouse skin was selected. All ratios represented by A/B, or A/B/C, and all percentages are by weight. The compounds described as $C_{12\text{-}18}OH$ are the straight chain, saturated, normal alcohols. EtOH is ethanol. The term mcg=microgram.

EXAMPLE 2

| Vehicle | mcg/cm$^2$ (0–24 hrs.)* |
|---|---|
| .5% Triamcinolone in a vehicle of Propylene Glycol | 0.4 |
| .5% Triamcinolone in a vehicle of 98% Propylene Glycol + 2% $C_{14}OH$ | 11 |
| .5% Triamcinolone in a vehicle of 95% Propylene Glycol + 5% Oleic Acid | 172 |

EXAMPLE 3

| Vehicle | mcg/cm$^2$ (0–8 hrs.)** |
|---|---|
| .5% Triamcinolone in a vehicle of Propylene Glycol | 0.35 |
| .5% Triamcinolone in a vehicle of 95% Propylene Glycol + 5% Oleic Acid | 45 |

EXAMPLE 4

| Vehicle | mcg/cm$^2$ (0–8 hrs.)** |
|---|---|
| .5% Triamcinolone in a vehicle of Propylene Glycol | 0.21 |
| .1% Triamcinolone in a vehicle of Oleic Acid | 1.8 |
| .5% Triamcinolone in a vehicle of 99% Propylene Glycol + 1% Oleic Acid | 23 |
| .5% Triamcinolone in a vehicle of | 46 |

-continued

| Vehicle | mcg/cm$^2$ (0–8 hrs.)** |
|---|---|
| 95% Propylene Glycol + 5% Oleic Acid | |
| .4% Triamcinolone in a vehicle of | 39 |
| 75% Propylene Glycol + 25% Oleic Acid | |

EXAMPLE 5

| Vehicle | mcg/cm$^2$ (0–6 hrs.)** |
|---|---|
| .1% Triamcinolone in a vehicle of 20/80 Propylene Glycol/EtOH | 0.17 |
| .1% Triamcinolone in a vehicle of 15/5/80 Propylene Glycol/Oleic Acid/EtOH | 2.65 |
| .1% Triamcinolone in a vehicle of 15/5/80 Propylene Glycol/Methyl laurate/EtOH | 2.73 |
| .1% Triamcinolone in a vehicle of 15/5/80 Propylene Glycol/C$_{14}$OH/EtOH | 1.40 |
| .1% Triamcinolone in a vehicle of 15/5/80 Propylene Glycol/Monoolein/EtOH | 0.49 |
| .1% Triamcinolone in a vehicle of 15/5/80 Propylene Glycol/Azone/EtOH | 1.87 |

EXAMPLE 6

| Vehicle | mcg/cm$^2$ (0–4 hrs.)** |
|---|---|
| .1% Triamcinolone in a vehicle of 20/80 Propylene Glycol/EtOH | 0.94 |
| .1% Triamcinolone in a vehicle of 15/5/80 Propylene Glycol/Oleic Acid/EtOH | 6.4 |
| .1% Triamcinolone in a vehicle of 15/5/80 Propylene Glycol/Linoleic Acid/EtOH | 5.4 |
| .1% Triamcinolone in a vehicle of 15/5/80 Propylene Glycol/Oleyl Alcohol/EtOH | 3.1 |
| .1% Triamcinolone in a vehicle of 15/5/80 Propylene Glycol/Linoleyl Alcohol/EtOH | 5.3 |

EXAMPLE 7

| Vehicle | mcg/cm$^2$ (0–70 hrs.)* |
|---|---|
| .1% Triamcinolone in a vehicle of 20/80 Propylene Glycol/EtOH | .29 |
| .1% Triamcinolone in a vehicle of 15/5/80 Propylene Glycol/Methyl Laurate/EtOH | 1.6 |
| 1% Hydrocortisone in a vehicle of 20/80 Propylene Glycol/EtOH | 2.8 |
| 1% Hydrocortisone in a vehicle of 15/5/80 Propylene Glycol/Methyl Laurate/EtOH | 5.4 |
| 1% Hydrocortisone in a vehicle of 15/5/80 Propylene Glycol/Oleic Acid/EtOH | 13.0 |
| 1% Hydrocortisone in a vehicle of 15/5/80 Propylene Glycol/C$_{14}$OH/EtOH | 8.8 |

EXAMPLE 8

The following Example demonstrates the dramatic reduction in penetration that takes place when the penetration-inhibiting compound described herein are added to compositions of the present invention.

| Vehicle | mcg/cm$^2$ (0–72 hrs.)* |
|---|---|
| 1% Triamcinolone in a vehicle of Propylene Glycol | .1 |
| 1% Triamcinolone in a vehicle of 98% Propylene Glycol + 2% C$_{14}$OH | 30 |
| 1% Triamcinolone in a vehicle of 94% Propylene Glycol + 2% C$_{14}$OH + 4% Octanoic Acid | 15 |

As can be seen from this example, the addition of a proscribed compound such as straight chain, normal $C_8$ monocarboxylic acid (octanoic acid), reduces penetration by 50%. Substantially similar results occur with addition of decanoic acid, cetyl alcohol or steryl alcohol.

EXAMPLE 9

| Vehicle | mcg/cm$^2$ (24 hrs.)* |
|---|---|
| .1% Triamcinolone in Propylene Glycol vehicle | 23 |
| .1% Triamcinolone in a vehicle of Propylene Glycol + 3% Oleic Acid | 72 |
| .1% Triamcinolone in a vehicle of Propylene Glycol + 3% C$_{12}$OH | 56 |
| .1% Triamcinolone in a vehicle of Propylene Glycol + 3% C$_{14}$OH | 36 |
| .1% Triamcinolone in a vehicle of Propylene Glycol + 3% C$_{16}$OH | 14 |
| .1% Triamcinolone in a vehicle of Propylene Glycol + 3% C$_{18}$OH | 20 |
| .1% Triamcinolone in a vehicle of Propylene Glycol + 3% Oleyl Alcohol | 56 |
| .1% Triamcinolone in a vehicle of Propylene Glycol/PEG 400 | 6 |

EXAMPLE 10

| Component | | mcg/cm$^2$ @ 24 hrs. | mcg/cm$^2$* @ 48 hrs. |
|---|---|---|---|
| Triamcinolone | 0.1% | 11.2 | 20.8 |
| Methyl Laurate | 5.0% | | |
| Propylene Glycol | 25.0% | | |
| EtOH | 30.0% | | |
| Carbopol 934[1] | 1.0% | | |
| TEA (triethanol amine) | 0.3% | | |
| Tween 80[2] | 0.2% | | |
| Water qs | 38.4% | | |

[1]Carbopol 934 is a polyacrylic acid polymer available from B.F. Goodrich
[2]Tween 80 is a nonionic, liquid sorbitan monooleate available from ICI Americas

EXAMPLE 11

| Component | | mcg/cm$^2$ @ 24 hrs. | mcg/cm$^2$* @ 48 hrs. |
|---|---|---|---|
| Triamcinolone | 0.1% | 12.5 | 37.0 |
| Oleic Acid | 2.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 41.4% | | |

EXAMPLE 12

| Component | | mcg/cm² @ 24 hrs. | mcg/cm²* @ 48 hrs. |
|---|---|---|---|
| Triamcinolone | 0.1% | 20.7 | 50.9 |
| Oleic Acid | 4.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 39.4% | | |

EXAMPLE 13

| Component | | mcg/cm² @ 24 hrs. | mcg/cm²* @48 hrs. |
|---|---|---|---|
| Hydrocortisone | 1.0% | 56.3 | 104.7 |
| Methyl Laurate | 5.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 37.5% | | |

EXAMPLE 14

| Component | | mcg/cm² @ 24 hrs. | mcg/cm²* @ 48 hrs. |
|---|---|---|---|
| Hydrocortisone | 1.0% | 42.5 | 91.6 |
| Oleic Acid | 2.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 40.5% | | |

EXAMPLE 15

| Component | | mcg/cm² @ 24 hrs. | mcg/cm²* @ 48 hrs. |
|---|---|---|---|
| Hydrocortisone | 1.0% | 51.8 | 129.6 |
| Oleic Acid | 4.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 38.5% | | |

EXAMPLE 16

| Component | | mcg/cm² @ 24 hrs. | mcg/cm²* @ 48 hrs. |
|---|---|---|---|
| Hydrocortisone | 1.0% | 53.9 | 136.7 |
| Methyl Laurate | 5.0% | | |
| 1-(2-hydroxyethyl)-aza-cyclopentan-2-one | 20.0% | | |
| EtOH | 30.0% | | |
| Carbopol 934 | 1.0% | | |
| TEA | 0.3% | | |
| Tween 80 | 0.2% | | |
| Water qs | 42.5% | | |

EXAMPLE 17

| Component | | mcg/cm² @ 24 hrs. | mcg/cm²* @ 48 hrs. |
|---|---|---|---|
| Triamcinolone | 0.1% | 1.69 | 4.31 |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 43.4% | | |

EXAMPLE 18

| Component | | mcg/cm² @ 24 hrs. | mcg/cm²* @ 48 hrs. |
|---|---|---|---|
| Hydrocortisone | 1.0% | 5.96 | 12.7 |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 42.5% | | |

EXAMPLE 19

| Component | | mcg/cm² @ 24 hrs. | mcg/cm²* @ 48 hrs. |
|---|---|---|---|
| Hydrocortisone | 1.0% | 5.71 | 18.8 |
| 1-(2-hydroxyethyl)aza-cyclopentan-2-one | 20.0% | | |
| EtOH | 30.0% | | |
| Carbopol 934 | 1.0% | | |
| TEA | 0.3% | | |
| Tween 80 | 0.2% | | |
| Water qs | 47.5% | | |

EXAMPLE 20

| Component | | mcg/cm² @ 24 hrs. | mcg/cm²* @ 48 hrs. |
|---|---|---|---|
| Triamcinolone | 0.1% | 1.44 | 5.75 |
| Propylene Glycol | 25.0% | | |
| EtOH | 74.9% | | |

EXAMPLE 21

| Component | | mcg/cm² @ 24 hrs. | mcg/cm²* @ 48 hrs. |
|---|---|---|---|
| Hydrocortisone | 1.0% | 6.48 | 18.3 |
| Propylene Glycol | 24.5% | | |
| EtOH | 74.5% | | |

EXAMPLE 22

| Vehicle | mcg/cm² (0-48 hrs.)* |
|---|---|
| .5% Triamcinolone in a vehicle of Propylene Glycol | .056 |
| .1% Triamcinolone in a vehicle of Oleic Acid | .92 |
| 4.5% Triamcinolone in a vehicle of Azone | .92 |
| .6% Triamcinolone in a vehicle of 50/50 | .45 |

-continued

| Vehicle | mcg/cm² (0-48 hrs.)* |
|---|---|
| Oleic Acid/Azone | |
| .5% Triamcinolone in a vehicle of Propylene Glycol + 5% Oleic Acid | 63.0 |
| .5% Triamcinolone in a vehicle of Propylene Glycol + 5% Azone | 8.4 |

EXAMPLE 23

| Vehicle | mcg/cm² (0-4 hrs.)** |
|---|---|
| 1% Triamcinolone in a vehicle of Propylene Glycol | .14 |
| 7.8% Triamcinolone in a vehicle of Azone | 8.5 |
| .05% Triamcinolone in a vehicle of Oleic Acid | .81 |
| .7% Triamcinolone in a vehicle of 50/50 Azone/Oleic Acid | 1.5 |
| 1% Triamcinolone in a vehicle of Propylene Glycol + 4% Azone | 8.2 |
| 1% Triamcinolone in a vehicle of Propylene Glycol + 4% Oleic Acid | 123.0 |

EXAMPLE 24

| Vehicle | mcg/cm² (0-22 hrs.)** |
|---|---|
| 1% Triamcinolone in a vehicle of Propylene Glycol | 2.45 |
| 7.8% Triamcinolone in a vehicle of Azone | 77 |
| .05% Triamcinolone in a vehicle of Oleic Acid | 11 |
| .7% Triamcinolone in a vehicle of 50/50 Azone/Oleic Acid | 14.8 |
| 1% Triamcinolone in a vehicle of Propylene Glycol + 4% Azone | 147 |
| 1% Triamcinolone in a vehicle of Propylene Glycol + 4% Oleic Acid | 254 |

EXAMPLE 25

| Vehicle | mcg/cm² (0-68 hrs.)* |
|---|---|
| 1% Triamcinolone in a vehicle of Propylene Glycol | .082 |
| 7.8% Triamcinolone in a vehicle of Azone | .6 |
| 0.5% Triamcinolone in a vehicle of Oleic Acid | .089 |
| .7% Triamcinolone in a vehicle of 50/50 Oleic Acid/Azone | .22 |
| 1% Triamcinolone in a vehicle of Propylene Glycol + 4% Oleic Acid | 10.5 |
| 1% Triamcinolone in a vehicle of Propylene Glycol + 4% Azone | 2.1 |

EXAMPLE 26

The following Skin Pentration Study demonstrates the dramatic increase in penetration of a pharmaceutically-active agent (here Triamcinolone) when the binary combination of diol+Azone is employed, when compared to a vehicle containing just Azone, or just the diol, and a compatable volatile solvent. The following penetration study further demonstrates the criticality of the levels required by the present invention.

| Vehicle | mcg/cm² (24 hrs.)* |
|---|---|
| 0.1% Triamcinolone in a vehicle of 95/5 Ethanol/Azone | .85 |
| 0.1% Triamcinolone in a vehicle of 85/10/5 Ethanol/Propylene Glycol/Azone | .85 |
| 0.1% Triamcinolone in a vehicle of 75/20/5 Ethanol/Propylene Glycol/Azone | 1.5 |
| 0.1% Triamcinolone in a vehicle of 55/40/5 Ethanol/Propylene Glycol/Azone | 3.0 |
| 0.1% Triamcinolone in a vehicle of 75/20/5 Ethanol/Propylene Glycol/Oleic Acid | 5.2 |
| 0.1% Triamcinolone in a vehicle of 80/20 Ethanol/Propylene Glycol | 0.37 |

EXAMPLE 27

| Vehicle | mcg/cm²(0-48 hrs.)* |
|---|---|
| .1% Triamcinolone in a vehicle of 20/80 Propylene Glycol/EtOH | .12 |
| .1% Triamcinolone in a vehicle of 20/80 Pyrrolidone/EtOH | 3.5 |
| .1% Triamcinolone in a vehicle of 15/5/80 Propylene Glycol/Oleic Acid/EtOH | 5.4 |
| .1% Triamcinolone in a vehicle of 15/5/80 Pyrrolidone/Oleic Acid/EtOH | 9.9 |

EXAMPLE 28

| Vehicle | mcg/cm²(0-50 hrs.)* |
|---|---|
| 0.1% Triamcinolone in a vehicle of 20/80 Propylene Glycol/EtOH | .8 |
| 0.1% Triamcinolone in a vehicle of 20/80 Hydroxyethylpyrrolidone/EtOH | 1.1 |
| 0.1% Triamcinolone in a vehicle of 20/80 Pyrrolidone/EtOH | 3.4 |
| 0.1% Triamcinolone in a vehicle of 15/5/80 Propylene Glycol/Oleic Acid/EtOH | 3.3 |
| 0.1% Triamcinolone in a vehicle of 15/5/80 Pyrrolidone/Oleic Acid/EtOH | 5.9 |
| 0.1% Triamcinolone in a vehicle of 15/5/80 Hydroxyethylpyrrolidone/Oleic Acid/EtOH | 11.6 |

EXAMPLE 29

| Vehicle | mcg/cm² (0-65 hrs.)* |
|---|---|
| .1% Triamcinolone in a vehicle of 20/80 Propylene Glycol/EtOH | .27 |
| .1% Triamcinolone in a vehicle of 15/5/80 Propylene Glycol/Methyl laurate/EtOH | 1.5 |
| .1% Triamcinolone in a vehicle of 20/80 Hydroxyethylpyrrolidone/EtOH | .29 |
| .1% Triamcinolone in a vehicle of 15/5/80 Hydroxyethylpyrrolidone/Methyl laurate/EtOH | 3.6 |
| .1% Triamcinolone in a vehicle of 20/80 Hydroxypropylpyrrolidone/EtOH | .10 |
| .1% Triamcinolone in a vehicle of 15/5/80 Hydroxypropylpyrrolidone/Methyl laurate/EtOH | .81 |
| .1% Triamcinolone in a vehicle of 20/80 Methyl Pyrrolidone/EtOH | 1.3 |

-continued

| Vehicle | mcg/cm² (0–65 hrs.)* |
|---|---|
| .1% Triamcinolone in a vehicle of 15/5/80 Methyl Pyrrolidone/Methyl laurate/EtOH | 3.4 |

EXAMPLE 30

| Vehicle | mcg/cm² (0–48 hrs.)* |
|---|---|
| 1% Hydrocortisone in a vehicle of 20/80 Propylene Glycol/EtOH | 7.5 |
| 1% Hydrocortisone in a vehicle of 15/5/80 Propylene Glycol/Methyl laurate/EtOH | 17.0 |
| 1% Hydrocortisone in a vehicle of 15/5/80 Propylene Glycol/Oleic Acid/EtOH | 19.0 |
| 1% Hydrocortisone in a vehicle of 20/80 Hydroxyethylpyrrolidone/EtOH | 14.0 |
| 1% Hydrocortisone in a vehicle of 15/5/80 Hydroxyethylpyrrolidone/Oleic Acid/EtOH | 120.0 |

EXAMPLE 31

| Vehicle | mcg/cm² (0–48 hrs.)* |
|---|---|
| 1% Hydrocortisone in a vehicle of 20/80 Propylene Glycol/EtOH | 7.6 |
| 1% Hydrocortisone in a vehicle of 15/5/80 Propylene Glycol/Methyl laurate/EtOH | 33.0 |
| 1% Hydrocortisone in a vehicle of 20/80 Hydroxyethylpyrrolidone/EtOH | 8.3 |
| 1% Hydrocortisone in a vehicle of 15/5/80 Hydroxyethylpyrrolidone/Oleic Acid/EtOH | 124.0 |

What is claimed is:

1. A penetration-enhancing pharmaceutical composition for topical application comprising:
   (a) about 0.01% to about 10%, by weight, of a non-steroidal anti-inflammatory agent selected from the group consisting of salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, indomethacin, piroxicam, and mixtures thereof;
   (b) 0% to about 80% by weight of a solvent selected from ethanol and 2-propanol;
   (c) 0% to about 80% by weight water;
   (d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentan-2-one, and mixtures thereof; and
   (e) about 1.0% to about 35% by weight 1-dodecylazacycloheptan-2-one.

2. A composition according to claim 1 wherein the ratio by weight of component (d) to 1-dodecylazacycloheptan-2-one is from about 1:5 to about 100:1.

3. A composition according to claim 2 wherein the ratio by weight of component (d) to 1-dodecylazacycloheptan-2-one is from about 3:1 to about 100:1.

4. A penetration-enhancing pharmaceutical composition for topical application comprising:
   (a) about 0.01% to about 10%, by weight, of a corticosteroid selected from the group consisting of triamcinolone acetonide, hydrocortisone acetate, betamethasone valerate, fluocinolone acetonide, flupamesone, or mixtures thereof;
   (b) 0% to about 80% by weight of a solvent selected from ethanol and 2-propanol;
   (c) 0% to about 80% by weight water;
   (d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentan-2-one, and mixtures thereof; and
   (e) about 1.0% to about 35% by weight 1-dodecylazacycloheptan-2-one.

5. A composition according to claim 1 wherein the non-steroidal anti-inflammatory agent is present at a level of about 0.05% to about 10% by weight.

6. A penetration-enhancing pharmaceutical composition for topical application comprising:
   (a) about 0.01% to about 10%, by weight, of an antiviral agent selected from the group consisting of idoxuridine, iododeoxy uridine, amantadine, methisazone, cytarabine, and mixtures thereof;
   (b) 0% to about 80% by weight of a solvent selected from ethanol and 2-propanol;
   (c) 0% to about 80% by weight water;
   (d) about 15% to about 99% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentan-2-one and mixtures thereof; and
   (e) about 1.0% to about 35% by weight 1-dodecylazacycloheptan-2-one.

7. A penetration-enhancing pharmaceutical composition for topical application comprising:
   (a) about 0.01% to about 10%, by weight, of an antiviral agent having the formula

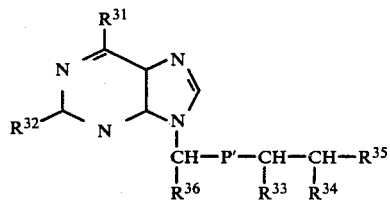

wherein P' is sulfur or oxygen, $R^{31}$ is hydrogen, a halogen, hydroxy, alkoxy, azide, thio, alkylthio, amino, alkylamino or dialkylamino; $R^{32}$ is hydrogen, a halogen alkylthio, acylamino, amino or azide; $R^{33}$ is hydrogen, a straight, branched or cyclic alkyl, hydroxyalkyl benzyloxyalkyl or phenyl; $R^{34}$ is hydrogen, hydroxy or alkyl; $R^{35}$ is hydrogen, hydroxy, amino, alkyl, hydroxyalkyl, benzyloxy, benzoyloxy, benzoyloxymethyl, sulfamoyloxy, phosphate carboxypropionyloxy, straight chain or cyclic acyloxyl having from 1 to 8 carbon atoms, or substituted carbamoyl group having the formula NHCO—Q; wherein Q is alkyl, aryl, or aralkyl optionally substituted by one or more substituents selected from sulfonyl, amino, carbamoyl or hydrogen; $R^{36}$ is hydrogen or an alkyl, provided that when P' is oxygen and $R^{32}$, $R^{33}$, $R^{34}$ and $R^{36}$ are H, $R^{31}$ is not amino or methylamino when $R^{35}$ is hydrogen or hydroxy, pharmaceutically-acceptable salts of these compounds, and mixtures thereof;
- (b) 0% to about 80% by weight of a solvent selected from ethanol and 2-propanol;
- (c) 0% to about 80% by weight water;
- (d) about 15% to about 99% by weight of a penetration-enhancing diol or cycloketo compound selected from the group consisting of 1,2-propanediol, 1,3-propanediol, 1,2-butanediol, pyrrolidone, 1-(2-hydroxyethyl)azacyclopentan-2-one, and mixtures there; and
- (e) about 1.0% to about 35% by weight 1-dodecylazacyloheptan-2-one.

8. A composition according to claim 7 wherein P' is sulfur or oxygen, $R^{31}$ is hydroxy, $R^{32}$ is amino, $R^{33}$ is hydrogen, a straight or branched chain or cyclic alkyl, hydroxyalkyl, benzyloxyalkyl or phenyl, $R^{34}$ is hydrogen, hydroxy or lower alkyl, $R^{35}$ is hydrogen, hydroxy amino, alkyl, hydroxyalkyl, benzoyloxy, benzoyloxy alkyl, benzyloxy, sulfamoyloxy, phosphate, carboxypropionyloxy, or acetoxy, $R^{36}$ is hydrogen, alkyl or hydroxyalkyl, or a pharmaceutically-acceptable salt of the above.

9. A composition according to claim 8 wherein the antiviral compound is 9-(2-hydroxyethoxymethyl)guanine, 2-amino-9-(2-hydroxyethoxymethyl)adenine, and mixtures thereof.

10. A composition according to claim 9 wherein the antiviral is 9-(2-hydroxyethoxymethyl)guanine.

11. A penetration-enhancing pharmaceutical composition for topical application comprising:
- (a) about 0.01% to about 10%, by weight, of a pharmaceutically-active antitussive agent selected from the group consisting of ephedrine, phenylpropanolamine, theophylline, codeine, pholcodine, hydrocodone, noscapine, dextromethorphan, levopropoxyphene, carbetapentane, pipazethate, isoaminile, chlorphendianol, benzonatate, dimemorphan and zipeprol, or mixtures thereof;
- (b) 0% to about 80% by weight of a solvent selected from ethanol and 2-propanol;
- (c) 0% to about 80% by weight water;
- (d) about 15% to about 99% by weight of a penetration-enhancing diol or cycloketo compound selected from the group consisting of 1,2-propanediol, 1,3-propanediol, 1,2-butanediol, pyrrolidone, 1-(2-hydroxyethyl)azacyclopentan-2-one, and mixtures thereof; and
- (e) about 1.0% to about 35% by weight 1-dodecylazacyloheptan-2-one.

12. A penetration-enhancing pharmaceutical composition for topical application comprising:
- (a) about 0.01% to about 10%, by weight, of a pharmaceutically-active bone-active organophosphate;
- (b) 0% to about 80% by weight of a solvent selected from ethanol and 2-propanol;
- (c) 0% to about 80% by weight water;
- (d) about 15% to about 99% by weight of a penetration-enhancing diol or cycloketo compound selected from the group consisting of 1,2-propanediol, 1,3-propanediol, 1,2-butanediol, pyrrolidone, 1-(2-hydroxyethyl)azacyclopentan-2-one, and mixtures thereof;
- (e) about 1.0% to about 35% by weight 1-dodecylazacyloheptan-2-one.

13. A composition according to claim 12 wherein the bone-active organophosphonate is selected from dichloromethanediphosphonic acid, ethane-1-hydroxy-1,1-diphosphonic acid, methane diphosphonic acid, the pharmaceutically-acceptable salts of these acids, and mixtures thereof.

14. A penetration enhancing pharmaceutical composition for topical application comprising:
- (a) about 0.01% to about 15% by weight of a sedative hypnotic or barbituate selected from the group consisting of amobarbital, aprobarbital, barbital, hexobarbital, mephobarbital, methohexital, pentobarbital, phenobarbital, probarbital, secobarbital, talbutal, thiamylal, thiopental, chlorodesmethyldiazepam, estazolam, flunitrazepam, flurazepam, fosazepam, lorazempam, nimetazepam, nitrazepam, nordiazepam, quazepam, triazolam, pyrithyldione, iminophenimide, ethinazone, mecloqualone, methaqualone, clomethizole, fenadiazole, ethinamate, hexapropymate, meprobamate, oxanamide, valnoctamide, butesamide, diethylallylacetamide, trimethobenzglycine, ibrotamide, capuride, ectylurea, apronalide, bromvalurea, acetylcarbromal, carbromal, amylene hydrate, chloretone, methylpentynol, brommethylpentynol, ethchlorvynol, methylphenylbutyndiol, paraldehyde, chloral hydrate and its derivatives, and mixtures thereof;
- (b) 0% to about 80% by weight of a solvent selected from ethanol and 2-propanol;
- (c) 0% to about 80% by weight water;
- (d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and
- (e) about 1.0% to about 35% by weight 1-dodecylazacycloheptan-2-one.

15. A penetration enhancing pharmaceutical composition for topical application comprising:
- (a) about 0.01% to about 10% by weight of an anti-anxiety agent selected from the group consisting of meprobamate, tybamate, phenprobamate, emylcamate, chlormezanone, nordiazepam, nitrazepam, diazepam, oxazepam, hemisuccinate, temazepam, camazepam, lorazepam, clonazepam, bromazepam, prazepam, flurazepam, chlordiazepoxide, demoxepam, clorazepate dipotassium, medazepam, triazolam, and mixtures thereof;
- (b) 0% to about 80% by weight of a solvent selected from ethanol and 2-propanol;
- (c) 0% to about 80% by weight water;
- (d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and
- (e) about 1.0% to about 35% by weight 1-dodecylazacycloheptan-2-one.

16. A penetration enhancing pharmaceutical composition for topical application comprising:
- (a) about 0.01% to about 10% by weight of an antihypertensive agent selected from the group consisting of clonidine, flutonidine, tolonidine, naphazoline, tetrahydrozoline, triamenidine, xylazine, guanabenz, alpha-methyldopa, metaraminol, methyloctopamine, dopamine-beta-hydroxylase, guanethidine sulfate, bethanidine, guanoxan, guanadrel, guanachlor, aminoethylguanines, debrisoquin, bretylium, phentolamine, tolazoline, phenoxybenzamine, prazosin, indoramine, nicergoline, methylapogalanthamine, propanolol, pindolol, alprenolol, oxprenolol, bunitrolol, tolamolol, practolol, atenolol, metoprolol, acebutolol, nadolol, timolol, satalol, and mixtures thereof;

(b) 0% to about 80% by weight of a solvent selected from ethanol and 2-propanol;

(c) 0% to about 80% by weight water;

(d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and (e) about 1.0% to about 35% by weight 1-dodecylazacycloheptan-2-one.

17. A penetration enhancing pharmaceutical composition for topical application comprising:

(a) about 0.01% to about 10% by weight of a cardiac drug selected from the group consisting of verapamil, guinidine, digitoxin, beta-methyldigoxin, digoxin, lanatoside C, lanthanum, lidocaine, propranolol, phenytoin, disopyramide, guinidine, procaine, procainamide, practolol, bretylium tosylate, aprindine, mexiletine, diphenidol, propafenone, tocainide, sodium nitrate, amyl nitrite, nitroglycerin, erythritol tetranitrate, pentaerythriol tetranitrate, mannitol hexanitrate, isosorbide dinitrate, trolnitrate phosphate, phentolamine, tolazoline, sodium nitroprusside, prazosin, hydralazine, varapamil HCl, diltiazem HCl, nifedipine, and mixtures thereof;

(b) 0% to about 80% by weight of a solvent selected from ethanol and 2-propanol;

(c) 0% to about 80% by weight water;

(d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and (e) about 1.0% to about 35% by weight 1-dodecylazacycloheptan-2-one.

18. A penetration enhancing pharmaceutical composition for topical application comprising:

(a) about 0.01% to about 10% by weight of a dieuretic or uricosuric selected from the group consisting of hydrochlorothiazides, bendroflumethiazide, benzthiazide, buthiazide, chlorothiazide, cyclopenthiazide, cyclothiazide, hydrochlorothiazide, hydroflumethiazide, methyclothiazide, polythiazide, trichlormethiazide, alipamide, chlorthalidone, clopamide, clorexolone, diapamide, mefruside, metolazone, quinethazone, chlorthalidones, 1-oxoisoindolines, ethacrynic acid, bumetanide, furosemide, indapamide, xipamide, piretanide, triflocin, muzolimine, 2-aminomethyl-3,4,6-trichlorophenol, etozolin, spironolactone, potassium canrenoate, potassium prorenoate, potassium mexrenoate, metyrapone, xanthines, aminouracils, 1-allyl-3-ethyl-6-aminouracil, amiloride, aminometradine, amisometradine, chlorazanil, clazolimine, aminophylline, triamterene, triazines, and mixtures thereof;

(b) 0% to about 80% by weight of a solvent selected from ethanol and 2-propanol;

(c) 0% to about 80% by weight water;

(d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and (e) about 1.0% to about 35% by weight 1-dodecylazacycloheptan-2-one.

19. A penetration enhancing pharmaceutical composition for topical application comprising:

(a) about 0.01% to about 10% by weight of a drug useful in treating neoplastic diseases selected from the group consisting of glutamine, folic acid, pyrimidine, purine antagonists, ribonucleoside diphosphonate and reductase inhibitors, nitrogen mustards, aziridines, methanesulfonic esters, 1,2-epoxides, nitrosoureas, triazenolimidazoles, procarbazine, mitotic inhibitors, hormones, L-asparaginase, mexthotrexate-5-fluoro-uracil, hexamethylmelamine, cis-dichlorodiamineplatinum (II), actinomycins, mithramycins, bleomycins, anthracyclines, and mixtures thereof;

(b) 0% to about 80% by weight of a solvent selected from ethanol and 2-propanol;

(c) 0% to about 80% by weight water;

(d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and (e) about 1.0% to about 35% by weight 1-dodecylazacycloheptan-2-one.

20. A penetration enhancing pharmaceutical composition for topical application comprising:

(a) about 0.01% to about 10% by weight of a local anesthetic selected from the group consisting of benzocaine, lidocaine, ketocaine, chloroprocaine, procain, ambucaine, propoxycaine, etidocaine, mepivacaine, prilocaine, quatracaine, tetracaine, tolcaine, aptocaine, bupivacaine, and mixtures thereof;

(b) 0% to about 80% by weight of a solvent selected from ethanol and 2-propanol;

(c) 0% to about 80% by weight water;

(d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and (e) about 1.0% to about 35% by weight 1-dodecylazacycloheptan-2-one.

21. A penetration enhancing pharmaceutical composition for topical application comprising:

(a) about 0.01% to about 10% by weight of an anorexigenic agent selected from the group consisting of amphetamine, dextroamphetamine, methamphetamine, benzphetamine, fenfluramine, chlorphentermine, chlortermine, phentermine, diethylpropion, phenylpropanolamine, 1-methyl-2-phenylmorpholine, phendimetrazine, phenmetrazine, mazindol, oxazolines, thioimidazolines, phenoxyalkyleneamines, biguanides, L-histidine, and mixtures thereof;

(b) 0% to about 80% by weight of a solvent selected from ethanol and 2-propanol;
(c) 0% to about 80% by weight water;
(d) about 25% to about 96% by weight of a penetration-enhancing diol or cycloketo compound selected from the group consisting of 1,2-propanediol, 1,3-propanediol, 1,2-butanediol, pyrrolidone, 1-(2-hydroxyethyl)-azacyclopentane-2-one, and mixtures thereof; and
(e) about 1.0% to about 35% by weight 1-dodecylazacycloheptan-2-one.

22. A composition according to claim 1 wherein said composition is substantially free of any single member of the saturated straight chain $C_{16}$–$C_{20}$ normal fatty alcohols or saturated straight chain $C_4$–$C_{20}$ mono- or dicarboxylic acids.

23. A composition according to claim 22 wherein said composition contains less than 3.5%, by weight, of any single member of the saturated, straight chain $C_{16}$–$C_{20}$ normal fatty alcohols or saturated straight chain $C_4$–$C_{20}$ mono- and dicarboxylic acids.

* * * * *